United States Patent
Johnson et al.

(10) Patent No.: US 10,166,315 B2
(45) Date of Patent: Jan. 1, 2019

(54) CHITOSAN-ENHANCED ELECTROSPUN FIBER COMPOSITIONS

(71) Applicant: NANOFIBER SOLUTIONS, INC., Hilliard, OH (US)

(72) Inventors: Jed Johnson, London, OH (US); Ronald Lloyd Bracken, Monroe, GA (US); Jason Chakroff, Columbus, OH (US)

(73) Assignee: NANOFIBER SOLUTIONS, INC., Hilliard, OH (US)

( * ) Notice: Subject to any disclaimer, the term of this patent is extended or adjusted under 35 U.S.C. 154(b) by 0 days.

(21) Appl. No.: 15/146,417

(22) Filed: May 4, 2016

(65) Prior Publication Data

US 2016/0325015 A1 Nov. 10, 2016

Related U.S. Application Data

(60) Provisional application No. 62/156,625, filed on May 4, 2015.

(51) Int. Cl.
*A61L 27/38* (2006.01)
*A61L 27/20* (2006.01)

(52) U.S. Cl.
CPC ........... *A61L 27/3834* (2013.01); *A61L 27/20* (2013.01); *A61L 2400/06* (2013.01); *A61L 2430/24* (2013.01)

(58) Field of Classification Search
None
See application file for complete search history.

(56) References Cited

U.S. PATENT DOCUMENTS

| | | |
|---|---|---|
| 4,738,740 A | 4/1988 | Pinchuk et al. |
| 5,258,027 A | 11/1993 | Berghaus |
| 5,628,788 A | 5/1997 | Pinchuk |
| 6,143,022 A | 11/2000 | Shull et al. |
| 7,115,220 B2 | 10/2006 | Dubson et al. |
| 7,172,765 B2 | 2/2007 | Chu et al. |
| 7,220,281 B2 | 5/2007 | Lambrecht et al. |
| 7,390,760 B1 | 6/2008 | Chen et al. |
| 7,413,575 B2 | 8/2008 | Phaneuf et al. |
| 7,490,563 B2 | 2/2009 | Eastin et al. |
| 7,629,030 B2 | 12/2009 | Robertson et al. |
| 7,718,351 B2 | 5/2010 | Ying et al. |
| 7,993,567 B2 | 8/2011 | Scott-Carnell et al. |
| 8,157,722 B2 | 4/2012 | Arnal et al. |
| 8,691,543 B2 | 4/2014 | Gaudette et al. |
| 8,771,582 B2 | 7/2014 | Phaneuf et al. |
| 8,932,683 B1 | 1/2015 | Kohlman et al. |
| 2002/0082707 A1 | 6/2002 | Homsy |
| 2002/0090725 A1 | 7/2002 | Simpson et al. |
| 2002/0142458 A1 | 10/2002 | Williams et al. |
| 2003/0168756 A1 | 9/2003 | Balkus, Jr. et al. |
| 2003/0226750 A1 | 12/2003 | Fenn |
| 2005/0177249 A1 | 8/2005 | Kladakis et al. |
| 2005/0277985 A1 | 12/2005 | Wert et al. |
| 2006/0060999 A1 | 3/2006 | Amagasa et al. |
| 2006/0085063 A1 | 4/2006 | Shastri et al. |
| 2006/0134157 A1 | 6/2006 | Lehman et al. |
| 2006/0135020 A1 | 6/2006 | Weinberg et al. |
| 2006/0154063 A1 | 7/2006 | Fujihara et al. |
| 2006/0200232 A1 | 9/2006 | Phaneuf et al. |
| 2006/0204539 A1 | 9/2006 | Atala et al. |
| 2007/0142907 A1 | 6/2007 | Moaddeb et al. |
| 2007/0191956 A1 | 8/2007 | Prewett et al. |
| 2007/0232169 A1 | 10/2007 | Strickler et al. |
| 2007/0269481 A1 | 11/2007 | Li et al. |
| 2007/0286880 A1 | 12/2007 | Vasiliev et al. |
| 2008/0208358 A1 | 8/2008 | Bellamkonda et al. |
| 2009/0018643 A1 | 1/2009 | Hashi et al. |
| 2009/0108503 A1 | 4/2009 | Scott-Carnell et al. |
| 2009/0143855 A1 | 6/2009 | Weber et al. |

(Continued)

FOREIGN PATENT DOCUMENTS

| | | |
|---|---|---|
| EP | 0416846 A2 | 3/1991 |
| EP | 2422003 | 10/2010 |

(Continued)

OTHER PUBLICATIONS

Mirahmadi et al., "Enhanced mechanical properties of thermosensitive chitosan hydrogel by silk fibers for cartilage tissue engineering", Materials Science and Engineering C 2013, vol. 33, pp. 4786-4794.*
Frey et al. "Electrospinning and Porosity Measurements of Nylon6 PEO blended Nonwovens" Journal of Engineered Fibers and Fabrics (2007), 2(1):31-37.
Hashi et al. "Antithrombogenic Modification of Small Diameter Microfibrous Vascular Grafts" Arterioscler Thromb Vasc Biol. (Aug. 2010), 30(8):1621-1627.
Meng et al., Journal of Nanoscience and Nanotechnology (Jul. 8, 2010), 312-320.
Ayres et al., "Microvascular Endothelial Cell Migration in Scaffolds of Electrospun Collagen," Wound Repair and Regeneration (Mar. 2005), 13(2):A6 (abstract only).
Abbott et al., "Effect of compliance mismatch on vascular graft patency" (1987) *J Vasc Surg*, 5(2):376-82.

(Continued)

*Primary Examiner* — Michelle F. Paguio Frising
(74) *Attorney, Agent, or Firm* — Pepper Hamilton LLP

(57) ABSTRACT

A composition may comprise a plurality of polymeric electrospun fiber fragments, and a carrier medium comprising an effective amount of chitosan. Such a composition may further include a plurality of polymeric electrospun fiber fragment clusters. A kit may comprise a first component of a plurality of polymeric electrospun fiber fragments, and a second component of a carrier medium comprising an effective amount of chitosan. A method of treatment may comprise injecting into a portion of a body a composition which may comprise a plurality of polymeric electrospun fiber fragments, and a carrier medium comprising an effective amount of chitosan. The treatment may be directed to one or more of joint inflammation, osteoarthritis, a tissue injury, a muscle tear, a ligament tear, a tendon tear, a void, incontinence, an aneurysm, and a tumor.

11 Claims, 15 Drawing Sheets

(56) References Cited

U.S. PATENT DOCUMENTS

| | | |
|---|---|---|
| 2009/0152773 A1 | 6/2009 | Barinov et al. |
| 2009/0162468 A1 | 6/2009 | Barinov et al. |
| 2009/0253328 A1 | 10/2009 | Watanabe et al. |
| 2010/0082114 A1 | 4/2010 | Gingras et al. |
| 2010/0105799 A1 | 4/2010 | Rudd et al. |
| 2010/0166854 A1 | 7/2010 | Michniak-Kohn et al. |
| 2010/0222771 A1 | 9/2010 | Mitchell et al. |
| 2010/0233115 A1 | 9/2010 | Patel et al. |
| 2010/0273258 A1 | 10/2010 | Lannutti et al. |
| 2010/0303881 A1 | 12/2010 | Hoke et al. |
| 2011/0022149 A1 | 1/2011 | Cox et al. |
| 2011/0028834 A1 | 2/2011 | Zussman |
| 2011/0030885 A1 | 2/2011 | Anneaux et al. |
| 2011/0070283 A1 | 3/2011 | Hossainy et al. |
| 2011/0083987 A1 | 4/2011 | Rolland et al. |
| 2011/0098826 A1 | 4/2011 | Mauck et al. |
| 2011/0166647 A1 | 7/2011 | Hashi et al. |
| 2011/0177395 A1 | 7/2011 | Kamisasa |
| 2011/0270412 A1 | 11/2011 | Bellan et al. |
| 2012/0068384 A1 | 3/2012 | Phaneuf et al. |
| 2012/0093717 A1 | 4/2012 | Mauck et al. |
| 2012/0271405 A1 | 10/2012 | Soletti et al. |
| 2013/0103079 A1 | 4/2013 | Lau et al. |
| 2013/0150963 A1 | 6/2013 | Johnson |
| 2013/0310920 A1 | 11/2013 | Su |
| 2014/0030315 A1 | 1/2014 | Johnson |
| 2014/0057346 A1 | 2/2014 | Johnson |
| 2014/0072951 A1 | 3/2014 | Johnson |
| 2014/0271795 A1 | 9/2014 | Phaneuf et al. |
| 2014/0272225 A1 | 9/2014 | Johnson |
| 2014/0309726 A1 | 10/2014 | Wang |
| 2017/0182206 A1 | 6/2017 | Johnson et al. |

FOREIGN PATENT DOCUMENTS

| | | | |
|---|---|---|---|
| JP | 2012-527217 A | 11/2012 | |
| WO | WO 2000/010622 A1 | 3/2000 | |
| WO | WO 2001/015754 A1 | 3/2001 | |
| WO | WO 2005/012606 A2 | 2/2005 | |
| WO | WO 2006/138552 A2 | 12/2006 | |
| WO | WO 2008/137659 A1 | 11/2008 | |
| WO | WO 2009/089035 A1 | 7/2009 | |
| WO | WO 2010/040129 A3 | 4/2010 | |
| WO | WO 2010/048281 A1 | 4/2010 | |
| WO | WO 2010/124207 A1 | 10/2010 | |
| WO | WO 2013/078051 A1 | 5/2013 | |
| WO | WO 2013/106822 A1 | 7/2013 | |
| WO | WO-2013152265 A1 * | 10/2013 | ............. A61L 27/56 |
| WO | WO 2014/031721 A1 | 2/2014 | |
| WO | WO 2014/145864 A1 | 9/2014 | |
| WO | WO-2014145002 A2 * | 9/2014 | ......... A61L 27/3604 |
| WO | WO 2015/153011 A1 | 10/2015 | |
| WO | WO 2015/187555 | 12/2015 | |

OTHER PUBLICATIONS

Abbott et al., Evaluation and Performance Standards for Arterial Prostheses, *Journal of Vascular Surgery* (Dec. 19, 1992), 17(4):746-756.
Aboitiz et al. "Fiber composition of the human corpus callosum" (Dec. 11, 1992) *Brain Res.* 598(1-2):143-153 (Abstract only).
Albertini et al. "The effect of glycosaminoglycans and proteoglycans on lipid peroxidation" (Aug. 2000) *Int. J. Mol. Med.* 6(2):129-136 (Abstract only).
Alexis et al. "In Vivo Particle Uptake by Airway Macrophages in Healthy Volunteers" (2006) *Am. J. Respir. Cell Mol. Biol.* 34(3):305-313.
Band et al. "Antiproliferative effect of gossypol and its optical isomers on human reproductive cancer cell lines" (Mar. 1989) *Gynecologic Oncology* 32(3):273-277 (Abstract only).
Bandtlow et al. "Proteoglycans in the developing brain: new conceptual insights for old proteins" (Oct. 2000) *Physiol. Rev.* 80(4):1267-1290.

Baran et al. "Important roles for macrophage colony-stimulating factor, CC chemokine ligand 2, and mononuclear phagocytes in the pathogenesis of pulmonary fibrosis" (2007) *Am. J. Respir. Crit. Care Med.* 176(1):78-89.
Bellail et al. "Microregional extracellular matrix heterogeneity in brain modulates glioma cell invasion" (Jun. 2004) *Int. J. Biochem. Cell Biol.* 36(6):1046-1069 (Abstract only).
Beningo et al. "Nascent Focal Adhesions Are Responsible for the Generation of Strong Propulsive Forces in Migrating Fibroblasts" (May 14, 2001) *J. Cell Biol.* 153(4):881-887.
Benz et al. "Biochemical Correlates of the Antitumor and Antimitochondrial Properties of Gossypol Enantiomers" (Jun. 1990) *Mol. Pharma.* 37(6):840-847 (Abstract only).
Benz et al. "Lactic Dehydrogenase Isozymes, $^{31}$P Magnetic-Resonance Spectroscopy, and In Vitro Antimitochondrial Tumor Toxicity With Gossypol and Rhodamine-123" (Feb. 1987) *J. Clin. Invest.* 79(2):517-523.
Benz et al. "Selective toxicity of gossypol against epithelial tumors and its detection by magnetic resonance spectroscopy" (Mar. 1988) *Contraception* 37(3):221-228 (Abstract only).
Berger et al., "Frequency of early occlusion and stenosis in a left internal mammary artery to left anterior descending artery bypass graft after surgery through a median sternotomy on conventional bypass: benchmark for minimally invasive direct coronary artery bypass" (1999) *Circulation*, 100(23):2353-8.
Bergmeister et al., "Electrospun Small-Diameter Polyurethane Vascular Grafts: Ingrowth and Differentiation of Vascular-Specific Host Cells" (2012) *Artificial Organs*, 36(1):54-61.
Bernstein et al. "Glioblastoma cells do not intravasate into blood vessels" (Jan. 1995) *Neurosurgery* 36(1):124-132 (Abstract only).
Bershadsky et al. "Adhesion-mediated mechanosensitivity: a time to experiment, and a time to theorize" (Oct. 2006) *Curr. Opn. Cell Biol.* 18(5):472-481 (Abstract only).
Binder et al. "Proteases and the Biology of Glioma Invasion" (2002) *J. Neuro-Oncology* 56:149-158.
Browning et al., "Multilayer vascular grafts based on collagen-mimetic proteins," (2012) *Acta Biomater* 8(3):1010-21.
Bucala et al. "Circulating Fibrocytes Define a New Leukocyte Subpopulation That Mediates Tissue Repair" (Nov. 1994) *Mol. Med.* 1(1):71-81 (Abstract only).
Camoretti-Mercado "Targeting the airway smooth muscle for asthma treatment" (Oct. 2009) *Translational Research* 154(4):165-174 (Abstract only).
Cattaruzza et al. "Proteoglycan control of cell movement during wound healing and cancer spreading" (Sep. 2005) *Matrix Biol.* 24(6):400-417 (Abstract only).
Central Brain Tumor Registry of the United States, Primary Brain Tumors in the United States—Statistical Report 1998-2002, *CBTRUS* 2005-2006.
Chalmers et al. "Chapter 9. Preparative applications of magnetic separation in biology and medicine" (2007) *Laboratory Techniques in Biochemistry and Molecular Biology* 32:249-264 (Abstract only).
Chen et al., Preparation and Characterization of Coaxial Electrospun Thermoplastic Polyurethane/Collagen Compound Nanofibers for Tissue Engineering Applications, *Colloids and Surfaces B-Biointerfaces* (2010), 79(2):315-325.
Chew et al. "The Role of Electrospinning in the Emerging Field of Nanomedicine" 2006, *Curr. Pharm. Sec.* 12(36)A:4751-4770.
Chicoine et al. "Assessment of brain-tumor cell motility in vivo and in vitro" (Apr. 1995) *J. Neurosurg.* 82(4):615-622 (Abstract only).
Choi et al. "Structuring electrospun polycaprolactone nanofiber tissue scaffolds by femtosecond laser ablation" (Nov. 2007) *J. Laser Appl.* 19(4):225-231.
Cleary et al., "Vascular tissue engineering: the next generation" (2012) Trends in Molecular Medicine 18(7):394-404.
Conte, "The ideal small arterial substitute: a search for the Holy Grail?" (1998) *FASEB J,.* 12(1):43-5.
Cukierman et al. "Taking cell-matrix adhesions to the third dimension" (Nov. 23, 2001) *Science* 294:1708-1712.
Dahl et al., "Readily Available Tissue-Engineered Vascular Grafts" (2011) *Science Translational Medicine*, 3(68).

(56) References Cited

OTHER PUBLICATIONS

Davis, et al. "Injectable biomaterials for the treatment of stress urinary incontinence: their potential and pitfalls as urethral bulking agents" (2013) Int Urogynecol J. 24:913-919.
Davies et al. "Adult axon regeneration in adult CNS white matter" (Dec. 1, 1998) Trends Neurosci. 21(12):515.
Davies and Hagen, "Pathophysiology of vein graft failure: a review" (1995) Eur J Vasc Endovasc Surg. 9(1):7-18.
Delpech et al. "Hyaluronan and hyaluronectin in the nervous system" (Sep. 28, 2007) Ciba Foundation Symposium 143—The Biology of Hyaluronan (Abstract only).
Diaz et al. "Controlled encapsulation of hydrophobic liquids in hydrophilic polymer nanofibers by co-electrospinning" (2006) Adv. Funct. Mater. 16(16):2110-2116.
Discher et al. "Tissue cells feel and respond to the stiffness of their substrate" (Nov. 18, 2005) Science 310:1139-1143.
Drilling et al. "Fabrication of burst pressure competent vascular grafts via electrospinning: Effects of microstructure" (Mar. 15, 2009) J. Miomed. Mat. Res. Part A 88A(4):923-934 (Abstract only).
Du et al., "Gradient nanofibrous chitosan/poly epsilon-caprolactone scaffolds as extracellular microenvironments for vascular tissue engineering" (2012) Biomaterials, 33(3):762-770.
Duling et al. "Mechanical characterization of electrospun Polycaprolactone (PCL): a potential scaffold for tissue engineering" (Feb. 2008) J. Biomech. Eng. 130(1) No. 011006 (Abstract only).
Engler et al. "Matrix Elasticity Directs Stem Cell Lineage Specification" (Aug. 25, 2006) Cell 126(4):677-689.
Epperly et al. "Correlation of Ionizing Irradiation-induced Late Pulmonary Fibrosis with Long-term Bone Marrow Culture Fibroblast Progenitor Cell Biology in Mice Homozygous Deletion Recombinant Negative for Endothelial Cell Adhesion Molecules" (2004) In Vivo 18(1):1-14.
Farin et al. "Transplanted glioma cells migrate and proliferate on host brain vasculature: a dynamic analysis" (Jun. 2006) Glia 53(8):799-808 (Abstract only).
Fathallah-Shaykh "Darts in the Dark Cure Animal, but Not Human, Brain Tumors" (May 2002) Arch. Neurol. 59:721-724 (Abstract only).
Ferraresso et al., "Early experience with a newly developed electrospun polycarbonate-urethane vascular graft for hemodialysis access" (2013) Journal of Vascular Access 14(3):252-256.
Fu et al., "Electrospun gelatin/PCL and collagen/PLCL scaffolds for vascular tissue engineering" (2014) International Journal of Nanomedicine, 9:2335-2344.
Fujiliara et al "Guided bone regeneration membrane made of Polycaprolactone/calcium carbonate composite nano-fibers" (Jul. 2005) Biomaterials 26(19):4139-4147 (Abstract only).
Furnari et al. "Malignant astrocytic glioma: genetics, biology, and paths to treatment" (2007) Genes Dev. 21:2683-2710.
Gaumer et al. "Structure-function relationships and Source-to-ground Distance and the Mechanical Properties of Electrospun Fiber" Acta Biomaterialia 5(5):1552-1561 (Abstract only).
Geiser et al. "The Role of Macrophages in the Clearance of Inhaled Ultrafme Titanium Dioxide Particles" (2008) Am. J. Respir. Cell Mol. Biol. 38(3):371-376.
Georges et al. "Cell type-specific response to growth on soft materials" (Apr. 2005) J. Appl. Physiol. 98:1547-1553.
Georges et al. "Matrices with compliance comparable to that of brain tissue select neuronal over glial growth in mixed cortical cultures" (Apr. 2006) Biophys. J. 90:3012-3018.
Giese et al. "Dichotomy of astrocytoma migration and proliferation" (1996) Int. J. Cancer 67:275-282.
Giese et al. "Glioma cell adhesion and migration on human brain sections" (1998) Anticancer Res. 18(4A):2435-2447 (Abstract only).
Giese et al. "Migration of Human Glioma Cells on Myelin" (Apr. 1996) Neurosurgery 38(4):755-764 (Abstract only).
Giese et al. "Substrates for astrocytoma invasion" (Aug. 1995) Neurosurgery 37(2):294-302 (Abstract only).

Gilbert et al. "Antiproliferative activity of gossypol and gossypolone on human breast cancer cells" (May 26, 1995) Life Sciences 57(1):61-67 (Abstract only).
Gladson "The Extracellular Matrix of Gliomas: Modulation of Cell Function" (Oct. 1999) J. Neuropath. Exper. Neur. 58(10):1029-1040 (Abstract only).
Goldbrunner et al. "Cell-extracellular matrix interaction in glioma invasion" (1999) Acta Neurochir (Wien) 141:295-305.
Goldman et al., "Radial artery grafts vs saphenous vein grafts in coronary artery bypass surgery: a randomized trial" (2011) Jama, 305(2):167-74.
Grandpre et al. "Nogo: a molecular determinant of axonal growth and regeneration" (Oct. 2001) Neuroscientist 7(5):377-386 (Abstract only).
Haley et al. "Study of myelin purity in relation to axonal contamination" (1980) Cell Mol. Neurobiol. 1:175-187.
Harrington et al., "Determining the fate of seeded cells in venous tissue-engineered vascular grafts using serial MRI" (2011) Faseb Journal, 25(12):4150-4161.
Hashi et al. "Antithrombogenic Property of Bone Marrow Mesenchymal Stem Cells in Nanofibrous Vascular Grafts" Jul. 17, 2007, PNAS 104(29) pp. 11915-11920.
He et al. "Fabrication of Drug-Loaded Electrospun Aligned Fibrous Threads for Suture Applications" 2009, J. Biomed. Mater. Research, Part A 89(1):80-95.
Hibino et al., "Tissue-engineered vascular grafts form neovessels that arise from regeneration of the adjacent blood vessel" (2011) Faseb Journal, 25(8):2731-2739.
Hibino et al., "A critical role for macrophages in neovessel formation and the development of stenosis in tissue-engineered vascular grafts" (2011) Faseb Journal, 25(12):4253-4263.
Hinz et al. "Alpha-smooth muscle actin expression upregulates fibroblast contractile activity" (Sep. 2001) Molecular Biology of the Cell 12(9):2730-2741.
Holland "Glioblastoma multiforme; the terminator" (Jun. 6, 2000) PNAS USA 97(12):6242-6244.
Hsu et al. "N,N-Dimethylformamide Additions to the Solution for the Electrospinning of Poly(ϵ-caprolactone) Nanofibers" (Apr. 2004) Macromolecular Materials and Engineering 289(4):334-340.
Hsu et al. "Nano-sized beads and porous fiber constructs of Poly(ϵ-caprolactone) produced by electrospinning" (2004) Journal of Material Science 39(9):3003-3013.
Hu et al. "Gossypol inhibits basal and estrogen-stimulated DNA synthesis in human breast carcinoma cells" (1993) Life Sciences 53(25):PL433-PL438 (Abstract only).
Hu et al. "Regulating axon growth within the postnatal central nervous system" (Dec. 2004) Semin Perinatol 28(6):371-378.
Hu et al. "The proteoglycan brevican binds to fibronectin after proteolytic cleavage and promotes glioma cell motility" (Sep. 5, 2008) Journal of Biological Chemistry 283(36):24848-24859.
Huang et al. "A review on polymer nanofibers by electrospinning and their applications in nanocomposites" (Nov. 2003) Composites Science and Technology 63(15):2223-2253 (Abstract only).
Huber et al., "Patency of autogenous and polytetrafluoroethylene upper extremity arteriovenous hemodialysis accesses: A systematic review " (2003) Journal of Vascular Surgery, 38(5):1005-1011.
Huynh et al., "Remodeling of an acellular collagen graft into a physiologically responsive neovessel" (1999) Nature Biotechnology, 17(11):1083-1086.
International Search Report and Written Opinion for PCT/US2015/016973 dated May 22, 2015.
Jaroszewski et al. "Action of Gossypol and Rhodamine 123 on Wild Type and Multidrug-resistant MCF-7 Human Breast Cancer Cells: $^{31}$P Nuclear Magnetic Resonance and Toxicity Studies" (1990) Cancer Research 50(21):6936-6943.
Johnson "First-in-the-World Equine Joint Injection for Osteoarthritis" (Jul./Aug. 2014) The International Equine Veterinarian 23-25.
Johnson et al. "Electrospun PCL in Vitro: a Microstructural Basis for Mechanical Property Changes" (2009) Journal of Biomaterials Science, Polymer Edition 20(4):467-481 (Abstract only).
Johnson et al. "Microstructure-Property Relationships in a Tissue-Engineering Scaffold" (2007) Journal of Applied Polymer Science 104(5):2919-2927.

(56) References Cited

OTHER PUBLICATIONS

Johnson et al. "Quantitative Analysis of Complex Glioma Cell Migration on Electrospun Polycaprolcatone Using Time-Lapse Microscopy" (2009) *Tissue Engineering Part C* 15(4):531-540.
Jung et al. "Tracking the invasiveness of human astrocytoma cells by using green fluorescent protein in an organotypical brain slice model" (Jan. 2001) *J. Neurosurgery* 94(1):80-89 (Abstract only).
Kang et al. Plasma Treatment of Textiles—synthetic Polymer-Base Textiles (2004) AATCC Review 4(11):29-33.
Kannan et al., "Current status of prosthetic bypass grafts: a review" (2005) *J Biomed Mater Res B Appl Biomater*, 74(1): 570-81.
Katta et al. "Continuous electrospinning of aligned polymer nanofibers onto a wire drum collector" (Sep. 28, 2004) *Nano Letters* 4(11):2215-2218 (Abstract only).
Kazemnejad et al. "Biochemical and Molecular Characterization of Hepatocyte-Like Cells Derived from Human Bone Marrow Mesenchymal Stem Cells on a Novel Three-Dimensional Biocompatible Nanofibrous Scaffold" Feb. 1, 2009, *J. Gastronenter. Hepatol.* 24(2):278-287.
Khil et al. "Novel fabricated matrix via electrospinning for tissue engineering" (2005) *Journal of Biomedical Materials Research Part B-Applied Biomaterials* 72B(1):117-124.
Kim et al. "Controlled protein release from electrospun biodegradable fiber mesh composed of poly(ε-caprolactone) and poly(ethylene oxide)" (Jun. 29, 2007) *International Journal of Pharmaceutics* 338 (1-2):276-283 (Abstract only).
Kim et al. "Epithelial cell α3β1 integrin links β-catenin and Smad signaling to promote myofibroblast formation and pulmonary fibrosis" (Jan. 2009) *Journal of Clinical Investigation* 119(1):213-224.
Kleihues et al. "The WHO Classification of Tumors of the Nervous System" (Mar. 2002) *J. Neuropathol. Exp. Neurol.* 61(3):215-225 (Abstract only).
Klim et al. "A Defined Glycosaminoglycan-Binding Substratum for Human Pluripotent Stem Cells" (2010) *Nature Methods* 7(23):989-996 (Abstract only).
Ko et al. "High Percentage of False-Positive Results of Cytokeratin 19 RT-PCR in Blood: A Model for the Analysis of Illegitimate Gene Expression" (2000) *Oncology* 59:81-88 (Abstract only).
Kwon et al. "Electrospun nano- to microfiber fabrics made of biodegradable copolyesters: structural characteristics, mechanical properties and cell adhesion potential" (Jun. 2005) *Biomaterials* 26(18):3929-3939.
Lannutti et al. "Electrospinning for tissue engineering scaffolds" (Apr. 2007) *Materials Science and Engineering: C* 27(3):504-509.
Leblanc et al. "An in vitro study of inhibitory activity of gossypol, a cottonseed extract, in human carcinoma cell lines" (Dec. 2002) *Pharmacological Research* 46(6):551-555.
Lee et al. "Characterization of nano-structured poly(ε-caprolactone) nonwoven mats via electrospinning" (Feb. 2003) *Polymer* 44(4):1287-1294.
Lesma et al. "Glycosaminoglycans in nerve injury: I. Low doses glycosaminoglycans promote neurite formation" (Dec. 1, 1996) *J. Neurosci. Res.* 46(5):565-571.
Levicar et al. "Proteases in brain tumour progression" (2003) *Acta Neurochir. (Wien.)* 145:825-838.
Levina et al. "Chemotherapeutic drugs and human tumor cells cytokine network" (2008) *International Journal of Cancer* 123(9):2031-2040.
L'Heureux et al. "Human tissue-engineered blood vessels for adult arterial revascularization" (2006) *Nature Medicine*, 12(3):361-365.
L'Heureux et al., "A completely biological tissue-engineered human blood vessel" (1998) *Faseb Journal*, 12(1):47-56.
L'Heureux et al., "Tissue-engineered blood vessel for adult arterial revascularization" (2007) *New England Journal of Medicine*, 357(14):1451-1453.
Li et al. "A three-dimensional nanofibrous scaffold for cartilage tissue engineering using human mesenchymal stem cells" (Feb. 2005) *Biomaterials* 26(6):599-609.
Li et al. "Biological response of chondrocytes cultured in three-dimensional nanofibrous poly(ε-caprolactone) scaffolds" (Dec. 15, 2003) *Journal of Biomedical Materials Research Part A* 67A(4):1105-1114.
Li et al. "Electrospinning nanofibers as uniaxially aligned arrays and layer-by-layer stacked films" (Feb. 2004) *Advanced Materials* 16(4):361-366.
Li et al. "Multilineage differentiation of human mesenchymal stem cells in a three-dimensional nanofibrous scaffold" (Sep. 2005) *Biomaterials* 26(25):5158-5166.
Liang et al. "Developing gossypol derivatives with enhanced antitumor activity" (1995) *Investigational New Drugs* 13(3):181-186.
Lieblein et al. "STAT3 can be activated through paracrine signaling in breast epithelial cells" (2008) *BMC Cancer* 8(302):1-14 :302.
Lin et al., "Small-caliber heparin-coated ePTFE grafts reduce platelet deposition and neointimal hyperplasia in a baboon model" (2004) *Journal of Vascular Surgery*, 39(6):1322-1328.
Lin et al., "Evaluation of platelet deposition and neointimal hyperplasia of heparin-coated small-caliber ePTFE grafts in a canine femoral artery bypass model" (2004) *Journal of Surgical Research*, 118(1):45-52.
Liu et al. "Function analysis of estrogenically regulated protein tyrosine phosphatase γ (PTPγ) in human breast cancer cell line MCF-7" (2004) *Oncogene* 23(6):1256-1262.
Liu et al. "Involvement of breast epithelial-stromal interactions in the regulation of protein tyrosine phosphatase-γ (PTPγ) mRNA expression by estrogenically active agents" (2002) *Breast Cancer Research and Treatment* 71(1):21-35.
Liu et al. The (-)-enantiomer of gossypol possesses higher anticancer potency than racemic gossypol in human breast cancer: (2002) *Anticancer Research* 22(1A):33-38.
Liu et al. "Transformation of MCF-10A Human Breast Epithelial Cells by Zeranol and Estradiol-17beta" (Nov.-Dec. 2004) *Breast J.* 10(6):514-521 (Abstract only).
Lo et al. "Cell movement is guided by the rigidity of the substrate" (Jul. 2000) *Biophysical Journal* 79(1);144-152.
Luu et al. "Development of a nanostructured DNA delivery scaffold via electrospinning of PLGA and PLGA and PLA-PEG block copolymers" (Apr. 29, 2003) *Journal of Controlled Release* 89(2):341-353.
Macchiarini et al. "Clinical Transplantation of a Tissue-Engineered Airway" (Dec. 13, 2008) *The Lancet* 372(9655):2023-2030.
Marelli et al., "Compliant electrospun silk fibroin tubes for small vessel bypass grafting" (2010) *Acta Biomaterialia*, 6(10):4019-4026.
Martins et al. "Electrospun nanostructured scaffolds for tissue engineering applications" (2007) Nanomedicine 2(6):929-942.
Mathew, "Preparation and anisotropic mechanical behavior of highly-oriented electrospun polybutylene terephthalate) fibers" (Aug. 2006) *Journal of Applied Polymer Science* 101(3):2017-2021.
McCallister et al., "Effectiveness of haemodialysis access with an autologous tissue-engineered vascular graft: a multicentre cohort study" (2009) *Lancet*, 373(9673):1440-1446.
McClure et al., "Electrospinning-aligned and random polydioxanone-polycaprolactone-silk fibroin-blended scaffolds: geometry for a vascular matrix" (2009) *Biomedical Materials*, 4(5).
McClure et al. "A Three-Layered Electrospun Matrix to Mimic Native Arterial Architecture Using Polycaprolactone, Elastin, and Collagen: A Preliminary Study" 2010, *Acta Biomaterialia* 6:2422-2433.
McKee et al., "Human arteries engineered in vitro" (2003) *EMBO Rep*, 4(6):633-8.
Mirensky et al., "Tissue-engineered arterial grafts: long-term results after implantation in a small animal model" (2009) *Journal of Pediatric Surgery*, 44(6): p. 1127-1133.
Morawski et al. "Perineuronal nets potentially protect against oxidative stress" (Aug. 2004) *Exp. Neurol.* 188(2):309-315.
Morgenstern et al. "Chondroitin sulphate proteoglycans in the CNS injury response" (2002) *Prog. Brain Res.* 137:313-332.
Mori et al. "Fibrocytes contribute to the myofibroblast population in wounded skin and originate from the bone marrow" (Mar. 10, 2005) *Experimental Cell Research* 304(1):81-90.

(56) References Cited

OTHER PUBLICATIONS

Murray et al. "Hyper-responsiveness of IPF/UIP fibroblasts: Interplay between TGF β1, IL-13 and CCL2" (2008) 40(10):2174-2182, International Journal of Biochemistry & Cell Biology.
Naito et al., "Characterization of the Natural History of Extracellular Matrix Production in Tissue-Engineered Vascular Grafts during Neovessel Formation" (2012) *Cells Tissues Organs*, 195(1-2):60-72.
Nam et al. "Improved Cellular Infiltration in Electrospun Fiber via Engineered Porosity" (Sep. 2007) *Tissue Engineering* 13(9):2249-2257.
Nam et al. "Materials selection and residual solvent retention in biodegradable electrospun fibers" (Feb. 5, 2008) *Journal of Applied Polymer Science* 107(3):1547-1524.
Nam et al. "Modulation of Embryonic Mesenchymal Progenitor Cell Differentiation via Control Over Pure Mechanical Modulus in Electrospun Nanofibers" (Apr. 2011) *Acta Biomaterialia* 7(4):1516-1524.
Nam et al. "Novel Electrospun Scaffolds for the Molecular Analysis of Chondrocytes Under Dynamic Compression" 2009, *Tissue Engineering Part A* 15(3):513-523.
Niklason et al., "Functional arteries grown in vitro. Science" (1999) 284(5413):489-493.
Ninomiya et al. "Transforming Growth Factor-β Signaling Enhances Transdifferentiation of Macrophages into Smooth Muscle-Like Cells" (2006) *Hypertension Research* 29(4):269-276.
Norton et al. "Myelination in rat brain: method of myelin isolation" (Oct. 1973) *J. Neurochem.* 21(4):749-757.
Novak et al. "Extracellular matrix and the brain: components and function" (2000) *J. Clin. Neurosci.* 7(4):280-290.
Ohnishi et al. "A Novel Model of Glioma Cell Invasion Using Organotypic Brain Slice Culture" (Jul. 15, 1998) *Cancer Res.* 58:2935-2940.
Palfi et al. "Correlation of in vitro infiltration with glioma histological type in organotypic brain slices" (2004) *Br. J. Cancer* 91(4):745-752.
Patterson et al., "Tissue-engineered vascular grafts for use in the treatment of congenital heart disease: from the bench to the clinic and back again" (2012) Regenerative Medicine, 2012. 7(3): p. 409-419.
Peck et al., "The Evolution of Vascular Tissue Engineering and Current State of the Art" (2012) *Cells Tissues Organs*, 195(1-2):144-158.
Pelham, Jr. et al. "Cell locomotion and focal adhesions are regulated by substrate flexibility" (Dec. 1997) *PNAS USA* 94:13661-13665.
Pham et al., Electrospinning of Polymeric Nanofibers for Tissue Engineering Applications: A Review, Tissue Engineering (2006), 12(5):1197-1211.
Pilkington "The paradox of neoplastic glial cell invasion of the brain and apparent metastatic failure" (1997) *Anticancer Res.* 17(6B):4103-4105 (Abstract).
Powell et al. "EDC cross-linking improves skin substitute strength and stability" (2006) *Biomaterials* 27(34): 5821-5827.
Prestwich et al., "What Is the Greatest Regulatory Challenge in the Translation of Biomaterials to the Clinic?" (2012) *Science Translational Medicine*, 4(160).
Properzi et al. "Proteoglycans and Brain Repair" (Feb. 2004) *News Physiol. Sci.* 19:33-38.
Quigley et al. "The relationship between survival and the extent of the resection in patients with supratentorial malignant gliomas" (1991) *Neurosurgery* 29:385-389.
Quint et al., "Allogeneic human tissue-engineered blood vessel"(2012) *Journal of Vascular Surgery*, 55(3):790-798.
Quint et al., "Decellularized tissue-engineered blood vessel as an arterial conduit" (Proceedings of the National Academy of Sciences of the United States of America, 2011. 108(22): p. 9214-9219.
Rao "Molecular mechanisms of glioma invasiveness: the role of proteases" (Jul. 2003) *Nature Reviews Cancer* 3:489-501.

Rath et al. "Compressive Forces Induce Osteogenic Gene Expression in Calvarial Osteoblasts" (2008) *Journal of Biomechanics* 41(5):1095-1103.
Rauch "Extracellular Rauch matrix components associated with remodeling processes in brain" (2004) *Cell Mol. Life Sci.* 61:203102045.
Reneker et al. "Nanometre diameter fibres of polymer, produced by electrospinning" (1996) *Nanotechnology* 7(3):216-223.
Rocks et al. "ADAMTS-1 Metalloproteinase Promotes Tumor Development through the Induction of a Stromal Reaction In vivo" (2008) *Cancer Research* 68(22):9541-9550.
Roger et al., "Heart disease and stroke statistics—2012 update: a report from the American Heart Association" (2012) Circulation, 125(1):e2-e220.
Roh et al., "Tissue-engineered vascular grafts transform into mature blood vessels via an inflammation-mediated process of vascular remodeling" (2010) *Proceedings of the National Academy of Sciences of the United States of America*, 107(10):4669-4674.
Rosamond et al., "Heart disease and stroke statistics—2008 update: a report from the American Heart Association Statistics Committee and Stroke Statistics Subcommittee" (2008) *Circulation* 117(4):e25-146.
Ruoslahti "Brain extracellular matrix" (1996) Glycobiologhy 6(5):489-492.
Salacinski et al., "The mechanical behavior of vascular grafts: a review" (2001) *J Biomater Appl*, 2001.15(3):241-78.
Sasmono et al. "A macrophage colony-stimulating factor receptor—green fluorescent protein transgene is expressed throughout the mononuclear phagocyte system of the mouse" (2003) *Blood* 101(3):1155-1163.
Saunders et al. "Fibrocyte localization to the airway smooth muscle is a feature of asthma" (Feb. 2009) *Journal of Allergy and Clinical Immunology* 123(2): 376-384.
Schiffer et al. "Cell proliferation and invasion in malignant gliomas" (1997) *Anticancer Research* 17(1A):61-69 (Abstract only).
Schmidt et al. "Identification of Circulating Fibrocytes as Precursors of Bronchial Myofibroblasts in Asthma" (2003) *Journal of Immunology* 171(1):380-389.
Shaw et al., "Determinants of coronary artery compliance in subjects with and without angiographic coronary artery disease" (2002) *Journal of the American College of Cardiology*, 39(10):1637-1643.
Shin et al. "Contractile cardiac grafts using a novel nanofibrous mesh" (Aug. 2004) *Biomaterials* 25(17):3717-3723.
Shin et al. "In Vivo Bone Tissue Engineering Using Mesenchymal Stem Cells on a Novel Electrospun Nanofibrous Scaffold" (Jul. 9, 2004) *Tissue Engineering* 10(1-2):33-41.
Sieben et al. "PCR artifacts in LOH and MSI analysis of microdissected tumor cells" (Nov. 2000) *Human Pathology* 31(11):1414-1419.
Silver et al. "Regeneration beyond the glial scar" (Feb. 2004) *Nature* 5:146-156.
Spagnuolo and Liu, "Fabrication and Degradation of Electrospun Scaffolds from L-Tyrosine-Bsed Polyurethane Blends for Tissue Engineering Applications" (Oct. 27, 2011) *ISRN Nanotechnology*, 2012(2012):1-11.
Srikar et al. "Desorption-limited mechanism of release from polymer nanofibers" (2008) *Langmuir* 24(3):965-974.
Stein et al. "Estimating the cell density and invasive radius of three-dimensional glioblastoma tumor spheroids grown in vitro" (Aug. 1, 2007) *Applied Optics* 46(22):5110-5118.
Stitzel et al. "Controlled Fabrication of a Biological Vascular Substitute" 2006, *Biomaterials* 27:1088-1094.
Subramanian et al. "Metastasis to and from the central nervous system—the 'relatively protected site'" (Aug. 2002) *The Lancet Oncology* 3(8):498-507.
Swanson et al. "A quantitative model for differential motility of gliomas in grey and white matter" (Oct. 2000) *Cell Proliferation* 33(5):317-329.
Swanson "Quantifying glioma cell growth and invasion in vitro" (2008) *Mathematical and Computer Modeling* 47:638-648.
Teo et al. "A review on electrospinning design and nanofibre assemblies" (2006) *Nanotechnology* 17(14):R89-R106.
Teo et al. "Electrospun fibre bundle made of aligned nanofibers over two fixed points" 2005 *Nanotechnology* 16:1878-1884.

(56) References Cited

OTHER PUBLICATIONS

Thomas et al. "Effects of gossypol on the cell cycle phases in T-47D human breast cancer cells" (Jul.-Aug. 1991) *Anticancer Research* 11(4):1469-1476 (Abstract only).
Tomizawa and Noishiki, "Evaluation and Performance Standards for Arterial Prostheses" (1995) *Journal of Vascular Surgery*, 21(3):542-543.
Tomlinson et al. "Loss of heterozygosity analysis: Practically and conceptually flawed?" (2002) *Genes Chromosomes & Cancer* 34:349-353.
Tonn et al. "Mechanisms of glioma cell invasion" (2003) *Acta Neurochir* Suppl 88: 163-167.
Toole "Hyaluronan and its binding proteins, the hyaladherins" (1990) *Curr. Opin. Cell Biol.* 2:839-844.
Tse, et al. "Current Status of Pipeline Embolization Device in the Treatment of Intracranial Aneurysms: A review" (Dec. 2013) *World Neurosurgery* 80(6): 829-835.
Tuszynski et al. "Differential cytotoxic effect of gossypol on human melanoma, colon carcinoma, and other tissue culture cell lines" (Feb. 1984) *Cancer Research* 44(2):768-771.
Van Meter et al. "The role of matrix metalloproteinase genes in glioma invasion: co-dependent and interactive proteolysis" (2001) *Journal of Neuro-Oncology* 53:213-235.
Veleva et al., "Interactions between endothelial cells and electrospun methacrylic terpolymer fibers for engineered vascular replacements" (2009) *Journal of Biomedical Materials Research Part A*, 91A(4): p. 1131-1139.
Viapiano et al. "BEHAB/brevican requires ADAMTS-mediated proteolytic cleavage to promote glioma invasion" (2008) *J. Neurooncol.* 88:261-272.
Viapiano et al. "From barriers to bridges: chondroitin sulfate proteoglycans in neuropathology" (Oct. 2006) *Trends Mol. Med.* 12(10):488-496.
Vuorinen et al. "Debulking or biopsy of malignant glioma in elderly people—a 12andomized study" (2003) *Acta Neurochir.* 145:5-10.
Wang et al. "Conjugated Linoleic Acid (CLA) Up-regulates the Estrogen-regulated Cancer Suppressor Gene, Protein Tyrosine Phosphatase γ (PTPγ), in Human Breast Cells" (2006) *Anticancer Research* 26(1A):27-34.
Wang et al. "Effect of gossypol on DNA synthesis and cell cycle progression of mammalian cells in vitro" (Jan. 1984) *Cancer Research* 44(1):35-38.
Wang et al. "Nanofibres and their Influence on Cells for Tissue Regeneration" (2005) *Aust. J. Chem.* 58(10):704-712.
Wang et al. "Increased Circulating Fibrocytes in Asthma with Chronic Airflow Obstruction" (2008) *Am. J. Respir. Crit. Care Med.* 178(6): p. 583-591.
Williams et al. "Anti-glioma effects of protein kinase inhibitors that simultaneously block invasion and proliferation" (Oct. 2007) Abstracts from 12$^{th}$ Annual Meeting of the Society for Neuro-Oncology 9: 486 ET-18 (Abstract only).
Wu et al. "Versican protects cells from oxidative stress-induced apoptosis" (Feb. 2005) *Matrix Biology* 24(1):3-13.
Wu et al. "An in vitro and in vivo study of antitumor effects of gossypol on human SW-13 adrenocortical carcinoma" (1986) *Cancer Research* 49(14):3754-3758.
Wykosky et al. "Soluble monomeric EphrinA1 is released from tumor cells and is a functional ligand for the EphA2 receptor" (2008) *Oncogene* 27(58):7260-7273.
Xie et al. "Encapsulation of protein drugs in biodegradable microparticles by co-axial electrospray" Jan. 15, 2008) *Journal of Colloid and Interface Science* 317(2):469-476.
Xie et al. "White matter inhibitors in CNS axon regeneration failure" (Feb. 2007) *Exp. Neurol.* 209(2):302-312.
Yamaguchi "Lecticans: organizers of the brain extracellular matrix" (2000) *Cell Mol. Life Sci.* 57:276-289.
Yang et al. "Integrin α1β1 and +2β1 are the key regulators of hepatocarcinoma cell invasion across the fibrotic matrix microenvironment" (Dec. 1, 2003) *Cancer Research* 63(23): 8312-8317.
Yoo et al. "Surface-Functionalized Electrospun Nanofibers for Tissue Engineering and Drug Delivery" Jan. 1, 2009, *Advanced Drug Delivery Reviews* 61:1033-1042.
Yosibmoto et al. "A biodegradable nanofiber scaffold by electrospinning and its potential for bone tissue engineering" (May 2003) *Biomaterials* 24(12):2077-2082.
Yu et al. "Production of submicrometer diameter fibers by two-fluid electrospinning" (Sep. 2004) *Adv. Mater.* 16(17):1562-1566.
Zborowski et al. "Red blood cell magnetophoresis" (Apr. 2003) *Biophysical Journal* 84:2638-2645.
Zeng et al. "Enzymatic degradation of poly(L-lactide) and poly(ε-caprolactone) electrospun fibers" (Dec. 15, 2004) *Macromolecular Bioscience* 4(12):1118-1125.
Zeng et al. "Ultrafine fibers electrospun from biodegradable polymers" (Jul. 25, 2003) *Journal of Applied Polymer Science* 89(4):1085-1092.
Zhang et al. "Electrospinning of gelatin fibers and gelatin/PCL composite fibrous scaffolds" (2005) *J. Biomed. Mater. Res. Part B: Appl. Biomater.* 72B(1):156-165.
Zhang et al. "Recent development of polymer nanofibers for biomedical and biotechnological applications" (2005) *Journal of Materials Science—Materials in Medicine* 16(10):933-946.
Zilla and Human, "Prosthetic vascular grafts: Wrong models, wrong questions and no healing" (2007) *Biomaterials*, 28(34):5009-5027.
International Search Report and Written Opinion for PCT/US2016/030058 dated Jul. 29, 2016.
Supplemental European Search Report and Written Opinion for EP15774154 dated Sep. 22, 2017.
International Search Report and Written Opinion for International Application No. PCT/US2016/060157 dated Jan. 31, 2017.
Lee et al., "Biomedical Applications of Magnetically Functionalized Organic/Inorganic Hybrid Nanofibers," International Journal of Molecular Sciences (Jun. 15, 2015), 16 pp. 13661-13677.
Samios et al., "In situ compatibilization of polyurethane with poly(ethylene terephthalate)," Department of Chemistry, European Polymer Journal (2000), 36 pp. 937-947.
Park, Lab-made organ implanted for first time (Jul. 14, 2017), CNN.com, <http://www.cnn.com/2011/HEALTH/07/07/trachea.transplant/index.html>.

* cited by examiner

CHITOSAN-ENHANCED ELECTROSPUN FIBER COMPOSITIONS

CROSS-REFERENCE TO RELATED APPLICATIONS

This application claims priority to and benefit of U.S. Provisional Application Ser. No. 62/156,625 filed May 4, 2015, entitled "Chitosan-Enhanced Electrospun Fiber Compositions," the disclosure of which is incorporated herein by reference in its entirety.

SUMMARY

In an embodiment, a composition may include a plurality of polymeric electrospun fiber fragments, and a carrier medium comprising an effective amount of chitosan. The composition may further include a plurality of polymeric electrospun fiber fragment clusters.

In an embodiment, a kit may include a first component comprising a plurality of polymeric electrospun fiber fragments, and a second component comprising a carrier medium comprising an effective amount of chitosan.

In an embodiment, a method of treatment may comprise injecting, into a portion of a body, a composition which may include a plurality of polymeric electrospun fiber fragments, and a carrier medium comprising an effective amount of chitosan.

In an embodiment, a composition which may comprise a plurality of polymeric electrospun fiber fragments, and a carrier medium comprising an effective amount of chitosan, may be used in the manufacture of a medicament for the treatment of joint inflammation, osteoarthritis, a tissue injury, a muscle tear, a ligament tear, a tendon tear, a void, incontinence, an aneurysm, or a combination thereof.

DETAILED DESCRIPTION

Figure 1A:
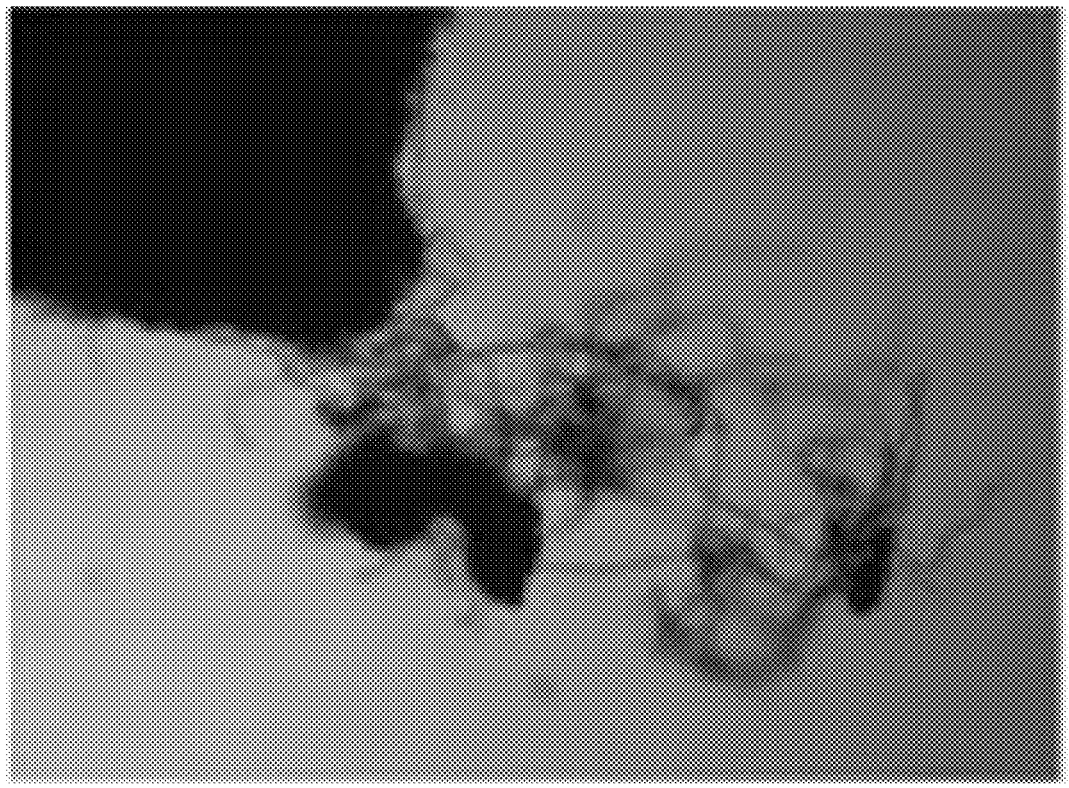
FIGS. 1A and 1B depict low-magnification and high-magnification images, respectively, of polymeric electrospun fiber fragments in accordance with the present disclosure.

Chitosan-enhanced electrospun fiber compositions are injectable compositions comprised of short fibers, or "nanowhiskers," suspended in a solution containing chitosan. Without wishing to be bound by theory, such fibers are thought to replicate the structure of native extracellular matrix (ECM), thereby allowing them to guide cell growth and direct phenotypic behavior. Electrospun fibers provide attachment sites for mesenchymal stem cells (MSCs) within, for example, the synovial fluid of an articular joint, thereby allowing chondrogenic differentiation to occur. Chitosan is a naturally derived long-chain polysaccharide that may help repair cartilage and other tissues. When chitosan is injected into arthritic joints, it may exhibit anti-inflammatory effects, increase the density of newly formed chondrocytes, suppress matrix metalloproteinase (MMP) expression, and enhance MSC attachment, proliferation, and viability. Chitosan may enhance chondrocyte attachment to bio-resorbable polyesters, cell adhesion, proliferation, and biosynthetic activity. The intraarticular injection of chitosan may increase epiphyseal cartilage in the tibial and femoral joints by activating chondrocyte proliferation. Importantly, when chitosan is added to an electrospun fiber composition, it may exhibit a synergistic effect that radically enhances the healing capacity of those electrospun fibers in applications for the treatment of osteoarthritis (OA) and the repair of soft tissue. The addition of chitosan to a composition of electrospun fibers surprisingly allows for a significant increase in the concentration of electrospun fibers in the composition without increased aggregation or clumping of those fibers. As a result, the injection or dispersion of electrospun fibers may be drastically improved by using chitosan to enhance such compositions. Cells can tightly attach to the chitosan and electrospun fiber fragments to form micromasses, which may grow into cartilage-like nodules. These fibers may be made of polymers, which may resorb within about 1 week to about 1 year following injection. In some examples, the fibers may resorb within about 6 weeks to about 8 weeks following injection. Without wishing to be bound by theory, these "nanowhiskers" may provide a biomimetic structure with physiologically relevant size and mechanical properties for cells to attach and proliferate. By micronizing fibers into small fragments and clusters, a very high surface area to volume ratio may be achieved. Such a surface area to volume ratio may support high density cell culture, which may result in increased cell production and reduced manufacturing costs. In some instances, such a surface area to volume ratio may be able to support up to 25 million cells in culture per milligram of "nanowhiskers."

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein and in the appended claims, the singular forms "a," "an," and "the" include plural references, unless the context clearly dictates otherwise. Thus, for example, reference to a "fiber" is a reference to one or more fibers and equivalents thereof known to those skilled in the art, and so forth.

As used herein, the term "about" means plus or minus 10% of the numerical value of the number with which it is being used. Therefore, about 50% means in the range of 40%-60%.

"Optional" or "optionally" means that the subsequently described event or circumstance may or may not occur, and that the description includes instances where the event occurs and instances where it does not.

As used herein, the term "therapeutic" describes an agent used to treat, combat, ameliorate, prevent or improve an unwanted condition or disease of a patient. In part, embodiments of the present disclosure are directed to the treatment of wounds, injuries of tendons, ligaments, or other musculoskeletal structures, blood vessels, organs, and the like.

When used in conjunction with a therapeutic, "administering" means to administer a therapeutic directly into or onto a target tissue, or to administer a therapeutic to a patient whereby the therapeutic positively impacts the tissue to which it is targeted. The compositions of the present disclosure can be administered in the conventional manner by any method in which they are effective. "Administering" may be accomplished by parenteral, intravenous, intramuscular, subcutaneous, intraperitoneal, intraarticular, or any other injection, oral or topical administration, suppository administration, inhalation, or by such methods in combination with other known techniques.

As used herein, the term "subject" includes, but is not limited to, humans, non-human vertebrates, and animals such as wild, domestic, and farm animals. In some embodiments, the term "subject" refers to mammals. In some embodiments, the term "subject" refers to humans.

A "therapeutically effective amount" or an "effective amount" of a composition is a predetermined amount calculated to achieve the desired effect, i.e., to improve, localize, increase, inhibit, block, or reverse the adhesion, activation, migration, penetration, or proliferation of cells. The activity contemplated by the present methods includes medical, therapeutic, cosmetic, aesthetic, and/or prophylactic treatment, as appropriate. The specific dose of a composition administered according to this disclosure to obtain therapeutic, cosmetic, aesthetic, and/or prophylactic effects will, of course, be determined by the particular circumstances surrounding the case, including, for example, the composition administered, the route of administration, and the condition being treated. The compositions disclosed herein are effective over a wide dosage range. It will be understood that the effective amount administered will be determined by the physician, veterinarian, or other medical professional in the light of the relevant circumstances including the condition to be treated, the choice of composition to be administered, and the chosen route of administration; therefore, the concentrations and dosage ranges described herein are not intended to limit the scope of the disclosure in any way.

The terms "treat," "treated," or "treating," as used herein, refer to both therapeutic treatment and prophylactic or preventative measures, wherein the object is to prevent or slow down (lessen) or entirely reverse (eradicate) an undesired physiological condition, disorder or disease, or to obtain beneficial or desired clinical results. For the purposes of this disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; remission (whether partial or total), whether detectable or undetectable, or enhancement or improvement of the condition, disorder, or disease; and eradication of the condition, disorder, or disease. Treatment includes eliciting a clinically significant response without excessive levels of side effects. Treatment also includes prolonging survival as compared to expected survival without treatment.

As used herein, the term "fragment" refers to a portion of a particular fiber. In some embodiments, a fragment may have an average length of about 1 µm to about 1000 µm, and an average diameter of about 0.1 µm to about 10 µm. In some embodiments, a composition may contain a plurality of fragments. Some non-limiting examples of average fragment lengths may include an average length of about 1 µm, about 5 µm, about 10 µm, about 20 µm, about 30 µm, about 40 µm, about 50 µm, about 75 µm, about 90 µm, about 95 µm, about 100 µm, about 105 µm, about 110 µm, about 150 µm, about 200 µm, about 300 µm, about 400 µm, about 500 µm, about 600 µm, about 700 µm, about 800 µm, about 900 µm about 1000 µm, or ranges between any two of these values (including endpoints). Some non-limiting examples of average fragment diameters may include an average diameter of about 0.1 µm, about 0.5 µm, about about 2 µm, about 3 µm, about 4 µm, about 5 µm, about 6 µm, about 7 µm, about 8 µm, about 9 µm, about 10 µm, or ranges between any two of these values (including endpoints).

When combined with a carrier medium, the resulting mixture may include from about 1 fragment per $mm^3$ to about 100,000 fragments per $mm^3$. Some non-limiting examples of mixture densities may include about 2 fragments per $mm^3$, about 100 fragments per $mm^3$, about 1,000 fragments per $mm^3$, about 2,000 fragments per $mm^3$, about 5,000 fragments per $mm^3$, about 10,000 fragments per $mm^3$, about 20,000 fragments per $mm^3$, about 30,000 fragments per $mm^3$, about 40,000 fragments per $mm^3$, about 50,000 fragments per $mm^3$, about 60,000 fragments per $mm^3$, about 70,000 fragments per $mm^3$, about 80,000 fragments per $mm^3$, about 90,000 fragments per $mm^3$, about 100,000 fragments per $mm^3$, or ranges between any two of these values (including endpoints).

As used herein, the term "cluster" refers to an aggregate of fiber fragments, or a linear or curved three-dimensional group of fiber fragments. Clusters may have a range of shapes. Non-limiting examples of cluster shapes may include spherical, globular, ellipsoidal, and flattened cylinder shapes. Clusters may have, independently, an average length of about 1 µm to about 1000 µm, an average width of about 1 µm to about 1000 µm, and an average height of about 1 µm to about 1000 µm. It may be appreciated that any cluster dimension, such as length, width, or height, is independent of any other cluster dimension. Some non-limiting examples of average cluster dimensions include an average dimension (length, width, height, or other measurement) of about 1 µm, about 5 µm, about 10 µm, about 20 µm, about 30 µm, about 40 µm, about 50 µm, about 75 µm, about 90 µm, about 95 µm, about 100 µm, about 105 µm, about 110 µm, about 150 µm, about 200 µm, about 300 µm, about 400 µm, about 500 µm, about 600 µm, about 700 µm, about 800 µm, about 900 µm, 1000 µm, or ranges between any two of these values (including endpoints), or independent combinations of any of these ranges of dimensions. Clusters may include an average number of about 2 to about 1000 fiber fragments. Some non-limiting examples of average numbers of fiber fragments per cluster include an average of about 2 fiber fragments per cluster, about 5 fiber fragments per cluster, about 10 fiber fragments per cluster, about 20 fiber fragments per cluster, about 30 fiber fragments per cluster, about 40 fiber fragments per cluster, about 50 fiber fragments per cluster, about 60 fiber fragments per cluster, about 70 fiber fragments per cluster, about 80 fiber fragments per cluster, about 90 fiber fragments per cluster, about 100 fiber fragments per cluster, about 110 fiber fragments per cluster, about 200 fiber fragments per cluster, about 300 fiber fragments per cluster, about 400 fiber fragments per cluster, about 500 fiber fragments per cluster, about 600 fiber fragments per cluster, about 700 fiber fragments per cluster, about 800 fiber fragments per cluster, about 900 fiber fragments per cluster, about 1000 fiber fragments per cluster, or ranges between any two of these values (including endpoints).

In some embodiments, a composition may contain a plurality of fragments. In some embodiments, a composition may contain a plurality of clusters. In some embodiments, a composition may contain a plurality of fragments and a plurality of clusters. In some embodiments, a composition may contain a plurality of fragments, a plurality of clusters, and, optionally, a carrier medium. In some embodiments, the carrier medium may include an effective amount of chitosan. In some embodiments, a composition may contain a plurality of fragments, a carrier medium, and, optionally, a plurality of cells. In some embodiments, a composition may contain a plurality of fragments, a plurality of clusters, a carrier medium, optionally, an effective amount of chitosan, and optionally, one or more biological cells.

As used herein, the term "chitosan" refers to a linear polysaccharide composed of randomly distributed β-(1-4)-linked D-glucosamine (deacetylated unit) and N-acetyl-D-glucosamine (acetylated unit). Chitosan may be derived from the treatment of crustacean shells with alkali sodium hydroxide. Chitosan may be produced by the deacetylation of chitin, which is a structural element in the exoskeleton of crustaceans and fungi. When chitosan is injected into arthritic joints, it may exhibit anti-inflammatory effects, increase the density of newly formed chondrocytes, suppress matrix metalloproteinase (MMP) expression, and enhance MSC attachment, proliferation, and viability. Chitosan may enhance chondrocyte attachment to bio-resorbable polyesters, cell adhesion, proliferation, and biosynthetic activity. The intraarticular injection of chitosan may increase epiphyseal cartilage in the tibial and femoral joints by activating chondrocyte proliferation. In some embodiments, a composition may contain a plurality of fragments, a plurality of clusters, and a carrier medium which may contain an effective amount of chitosan.

In some embodiments, the concentration of polymeric electrospun fiber fragments and, optionally, polymeric electrospun fiber fragment clusters, in the carrier medium may be from about 1 mg/mL to about 30 mg/mL. Some non-limiting examples of concentrations of polymeric electrospun fiber fragments and, optionally, clusters, in the carrier medium may include about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, or any range between any two of these values, including endpoints.

In some embodiments, a composition may contain a weight percent of chitosan to the carrier medium from about 0.001 wt % to about 5 wt %. Some non-limiting examples of weight percent of chitosan to carrier medium include about 0.001 wt %, about 0.01 wt %, about 0.1 wt %, about 0.5 wt %, about 0.5 wt %, about 1 wt %, about 1 wt %, about 1.5 wt %, about 1.5 wt %, about 2 wt %, about 2 wt %, about 2.5 wt %, about 2.5 wt %, about 3 wt %, about 3 wt %, about 3.5 wt %, about 3.5 wt %, about 4 wt %, about 4 wt %, about 4.5 wt %, about 4.5 wt %, about 5 wt %, or ranges between any two of these values (including endpoints).

In some embodiments, polymeric electrospun fibers, polymeric electrospun fiber fragments, or polymeric electrospun fiber fragment clusters may include one or more additional surface treatments which can be used to modulate and enhance cellular attachment to the polymeric electrospun fibers. In some embodiments, the surface treatments may include radio frequency plasma treatments, or equivalents known in the art. In other embodiments, the polymeric electrospun fibers, polymeric electrospun fiber fragments, or polymeric electrospun fiber fragment clusters may not cause untreatable inflammation or rejection when implanted in a patient. As such, in certain embodiments, the composition comprising polymeric electrospun fibers, polymeric electrospun fiber fragments, or polymeric electrospun fiber fragment clusters may not be subject to rejection or life-threatening inflammation within 1 day, 3 days, 5 days, 7 days, 2 weeks, 3 weeks, a month or longer after injection or implantation. In some embodiments, the composition comprising polymeric electrospun fibers, polymeric electrospun fiber fragments, or polymeric electrospun fiber fragment clusters may be retained in the patient for at least 1 day, 3 days, 5 days, 7 days, 2 weeks, 3 weeks, a month or longer. In certain embodiments, the composition may be retained in the patient for 6 months, a year, a term of years, or the lifetime of the patient.

Electrospinning Fibers

Electrospinning is a method which may be used to process a polymer solution into a fiber. In embodiments wherein the diameter of the resulting fiber is on the nanometer scale, the fiber may be referred to as a nanofiber. Fibers may be formed into a variety of shapes by using a range of receiving surfaces, such as mandrels or collectors. In some embodiments, a flat shape, such as a patch, sheet, or sheet-like fiber mold or fiber scaffold, may be formed by using a substantially round or cylindrical mandrel, and cutting and unrolling the resulting fiber mold to form the sheet. The resulting fiber molds or shapes may be used in many applications, including the repair or replacement of biological structures. In some embodiments, the resulting fiber scaffold may be implanted into a biological organism or a portion thereof. In other embodiments, the resulting fiber scaffold may be placed on or affixed to a wound or a portion thereof.

Electrospinning methods may involve spinning a fiber from a polymer solution by applying a high DC voltage potential between a polymer injection system and a mandrel. In some embodiments, one or more charges may be applied to one or more components of an electrospinning system. In some embodiments, a charge may be applied to the mandrel, the polymer injection system, or combinations or portions thereof. Without wishing to be bound by theory, as the polymer solution is ejected from the polymer injection system, it is thought to be destabilized due to its exposure to a charge. The destabilized solution may then be attracted to a charged mandrel. As the destabilized solution moves from the polymer injection system to the mandrel, its solvents may evaporate and the polymer may stretch, leaving a long, thin fiber that is deposited onto the mandrel. The polymer solution may form a Taylor cone as it is ejected from the polymer injection system and exposed to a charge.

In some embodiments, more than one polymer fiber may be electrospun simultaneously onto the same mandrel from more than one polymer solution, in a process sometimes referred to as "co-spinning."

Polymer Injection System

A polymer injection system may include any system configured to eject some amount of a polymer solution into an atmosphere to permit the flow of the polymer solution from the injection system to the mandrel. In some embodiments, the polymer injection system may deliver a continuous or linear stream with a controlled volumetric flow rate of a polymer solution to be formed into a fiber. In other embodiments, the polymer injection system may deliver a variable stream of a polymer solution to be formed into a fiber. In still other embodiments, the polymer injection system may be configured to deliver intermittent streams of a polymer solution to be formed into multiple fibers. In some embodiments, the polymer injection system may include a syringe under manual or automated control. In some embodiments, the polymer injection system may include multiple syringes and multiple needles or needle-like components under individual or combined manual or automated control. In some embodiments, a multi-syringe polymer injection system may include multiple syringes and multiple needles or needle-like components, with each syringe containing the same polymer solution. In some embodiments, a multi-syringe polymer injection system may include multiple syringes and multiple needles or needle-like components, with each syringe containing a different polymer solution. In other embodiments, the polymer injection system may comprise one or more polymer injection systems, such as a first polymer injection system, a second polymer injection system, a third polymer injection system, and so on. In some embodiments, a charge may be applied to the polymer injection system, or to a portion thereof. In some embodiments, a charge may be applied to a needle or needle-like component of the polymer injection system.

In some embodiments, the polymer solution may be ejected from the polymer injection system at a flow rate of less than or equal to about 5 mL/h. In other embodiments, the polymer solution may be ejected from the polymer injection system at a flow rate in a range from about 0.01 mL/h to about 50 mL/h. The flow rate at which the polymer solution is ejected from the polymer injection system may be, in some non-limiting examples, about 0.01 mL/h, about 0.05 mL/h, about 0.1 mL/h, about 0.5 mL/h, about 1 mL/h, 2 mL/h, about 3 mL/h, about 4 mL/h, about 5 mL/h, about 6 mL/h, about 7 mL/h, about 8 mL/h, about 9 mL/h, about 10 mL/h, about 11 mL/h, about 12 mL/h, about 13 mL/h, about 14 mL/h, about 15 mL/h, about 16 mL/h, about 17 mL/h, about 18 mL/h, about 19 mL/h, about 20 mL/h, about 21 mL/h, about 22 mL/h, about 23 mL/h, about 24 mL/h, about 25 mL/h, about 26 mL/h, about 27 mL/h, about 28 mL/h, about 29 mL/h, about 30 mL/h, about 31 mL/h, about 32 mL/h, about 33 mL/h, about 34 mL/h, about 35 mL/h, about 36 mL/h, about 37 mL/h, about 38 mL/h, about 39 mL/h, about 40 mL/h, about 41 mL/h, about 42 mL/h, about 43 mL/h, about 44 mL/h, about 45 mL/h, about 46 mL/h, about 47 mL/h, about 48 mL/h, about 49 mL/h, about 50 mL/h, or any range between any two of these values, including endpoints.

As the polymer solution travels from the polymer injection system toward the mandrel, the diameter of the resulting fibers may be in the range of about 0.1 µm to about 10 µm. Some non-limiting examples of electrospun fiber diameters may include about 0.1 µm, about 0.2 µm, about 0.5 µm, about 1 µm, about 2 µm, about 5 µm, about 10 µm, about 20 µm, or ranges between any two of these values, including endpoints. In some embodiments, the resulting fibers may be crushed, micronized, pulverized, or otherwise reduced to smaller fiber fragments and/or clusters.

Polymer Solution

In some embodiments, the polymer injection system may be filled with a polymer solution. In some embodiments, the polymer solution may comprise one or more polymers. In some embodiments, the polymer solution may be a fluid formed into a polymer liquid by the application of heat. A polymer solution may include synthetic or semi-synthetic polymers such as, without limitation, polyethylene terephthalate (PET), polyester, polymethylmethacrylate, polyacrylonitrile, silicone, polyurethane, polycarbonate, polyether ketone ketone, polyether ether ketone, polyether imide, polyamide, polystyrene, polyether sulfone, polysulfone, polyvinyl alcohol (PVA), polyvinyl acetate (PVAc), polycaprolactone (PCL), polylactic acid (PLA), polyglycolide (PGA), polyglycerol sebacic, polydiol citrate, polyhydroxy butyrate, polyether amide, polydiaxanone (PDO), poly (lactide-co-caprolactone) (PLCL), poly (lactide-co-glycolide), poly-L-lactide, and combinations or derivatives thereof. Alternative polymer solutions used for electrospinning may include natural polymers such as fibronectin, collagen, gelatin, hyaluronic acid, chitosan, or combinations thereof. It may be understood that polymer solutions may also include a combination of synthetic polymers and naturally occurring polymers in any combination or compositional ratio. In some non-limiting examples, the polymer solution may comprise a weight percent ratio of, for example, polyethylene terephthalate to polyurethane, from about 10% to about 90%. Non-limiting examples of such weight percent ratios may include 10%, 25%, 33%, 50%, 66%, 75%, 90%, or ranges between any two of these values, including endpoints.

In some embodiments, the polymer solution may comprise one or more solvents. In some embodiments, the solvent may comprise, for example, acetone, dimethylformamide, dimethylsulfoxide, N-methylpyrrolidone, N,N-dimethylformamide, Nacetonitrile, hexanes, ether, dioxane, ethyl acetate, pyridine, toluene, xylene, tetrahydrofuran, trifluoroacetic acid, hexafluoroisopropanol, acetic acid, dimethylacetamide, chloroform, dichloromethane, water, alcohols, ionic compounds, or combinations thereof. The concentration range of a polymer or polymers in a solvent or solvents may be, without limitation, from about 1 wt % to about 50 wt %. Some non-limiting examples of polymer concentration in solution may include about 1 wt %, 3 wt %, 5 wt %, about 10 wt %, about 15 wt %, about 20 wt %, about 25 wt %, about 30 wt %, about 35 wt %, about 40 wt %, about 45 wt %, about 50 wt %, or ranges between any two of these values, including endpoints.

In some embodiments, the polymer solution may also include additional materials. Non-limiting examples of such additional materials may include radiation opaque materials, contrast agents, electrically conductive materials, fluorescent materials, luminescent materials, antibiotics, growth factors, vitamins, cytokines, steroids, anti-inflammatory drugs, small molecules, sugars, salts, peptides, proteins, cell factors, DNA, RNA, or any other materials to aid in non-invasive imaging, or any combination thereof. In some embodiments, the radiation opaque materials may include, for example, barium, tantalum, tungsten, iodine, gadolinium, gold, platinum, bismuth, or bismuth (III) oxide. In some embodiments, the electrically conductive materials may include, for example, gold, silver, iron, or polyaniline.

In some embodiments, the additional materials may be present in the polymer solution in an amount from about 1 wt % to about 500 wt %. In some non-limiting examples, the additional materials may be present in the polymer solution in an amount of about 1 wt %, about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, about 100 wt %, about 125 wt %, about 150 wt %, about 175 wt %, about 200 wt %, about 225 wt %, about 250 wt %, about 275 wt %, about 300 wt %, about 325 wt %, about 350 wt %, about 375 wt %, about 400 wt %, about 425 wt %, about 450 wt %, about 475 wt %, about 500 wt %, or any range between any of these two values, including endpoints.

The type of polymer in the polymer solution may determine the characteristics of the electrospun fiber. Some fibers may be composed of polymers that are bio-stable and not absorbable or biodegradable when implanted. Such fibers may remain generally chemically unchanged for the length of time in which they remain implanted. Alternatively, fibers may be composed of polymers that may be absorbed or bio-degraded over time.

In some embodiments, a polymeric electrospun fiber may have a degradation rate. The degradation rate may be defined in a number of ways, including, for example, by the amount of time the fiber takes to degrade completely when exposed to a bodily tissue or fluid. In such embodiments, the degradation rate may be, for example, from about 1 day to about 24 months. Some non-limiting examples of degradation rates in terms of the amount of time the fiber takes to degrade completely when exposed to a bodily tissue or fluid include about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 1 month, about 1.5 months, about 2 months, about 2.5 months, about 3 months, about 3.5 months, about 4 months, about 4.5 months, about 5 months, about 5.5 months, about 6 months, about 6.5 months, about 7 months, about 7.5 months, about 8 months, about 8.5 months, about 9 months, about 9.5 months, about 10 months, about 10.5 months, about 11 months, about 11.5 months, about 12 months, about 12.5 months, about 13 months, about 13.5 months, about 14 months, about 14.5 months, about 15 months, about 15.5 months, about 16 months, about 16.5 months, about 17 months, about 17.5 months, about 18 months, about 18.5 months, about 19 months, about 19.5 months, about 20 months, about 20.5 months, about 21 months, about 21.5 months, about 22 months, about 22.5 months, about 23 months, about 23.5 months, about 24 months, or any range between any two of these values, including endpoints.

The fibers disclosed herein may act as an initial template or scaffold for the repair or replacement of organs and/or tissues. These organ or tissue templates or scaffolds may degrade in vivo once the tissues or organs have been replaced or repaired by natural structures and cells. It may be further understood that a polymer solution and its resulting electrospun fiber(s) may be composed of more than one type of polymer, and that each polymer therein may have a specific characteristic, such as bio-stability or biodegradability at a particular degradation rate.

Applying Charges to Electrospinning Components

In an electrospinning system, one or more charges may be applied to one or more components, or portions of components, such as, for example, a mandrel or a polymer injection system, or portions thereof. In some embodiments, a positive charge may be applied to the polymer injection system, or portions thereof. In some embodiments, a negative charge may be applied to the polymer injection system, or portions thereof. In some embodiments, the polymer injection system, or portions thereof, may be grounded. In some embodiments, a positive charge may be applied to the mandrel, or portions thereof. In some embodiments, a negative charge may be applied to the mandrel, or portions thereof. In some embodiments, the mandrel, or portions thereof, may be grounded. In some embodiments, one or more components or portions thereof may receive the same charge. In some embodiments, one or more components, or portions thereof, may receive one or more different charges.

The charge applied to any component of the electrospinning system, or portions thereof, may be from about −15 kV to about 30 kV, including endpoints. In some non-limiting examples, the charge applied to any component of the electrospinning system, or portions thereof, may be about −15 kV, about −10 kV, about −5 kV, about −3 kV, about −1 kV, about −0.01 kV, about 0.01 kV, about 1 kV, about 5 kV, about 10 kV, about 12 kV, about 15 kV, about 20 kV, about 25 kV, about 30 kV, or any range between any two of these values, including endpoints. In some embodiments, any component of the electrospinning system, or portions thereof, may be grounded.

Mandrel Movement During Electrospinning

During electrospinning, in some embodiments, the mandrel may move with respect to the polymer injection system. In some embodiments, the polymer injection system may move with respect to the mandrel. The movement of one electrospinning component with respect to another electrospinning component may be, for example, substantially rotational, substantially translational, or any combination thereof. In some embodiments, one or more components of the electrospinning system may move under manual control. In some embodiments, one or more components of the electrospinning system may move under automated control. In some embodiments, the mandrel may be in contact with or mounted upon a support structure that may be moved using one or more motors or motion control systems. The pattern of the electrospun fiber deposited on the mandrel may depend upon the one or more motions of the mandrel with respect to the polymer injection system. In some embodiments, the mandrel surface may be configured to rotate about its long axis. In one non-limiting example, a mandrel having a rotation rate about its long axis that is faster than a translation rate along a linear axis, may result in a nearly helical deposition of an electrospun fiber, forming windings about the mandrel. In another example, a mandrel having a translation rate along a linear axis that is faster than a rotation rate about a rotational axis, may result in a roughly linear deposition of an electrospun fiber along a linear extent of the mandrel.

Surgical Procedures

While the prior disclosed compositions of non-textile implants are not within the scope of the disclosure, certain other methods, including surgical methods, can be easily adapted for use with the disclosed compositions. For example, a subject may be evaluated using one or more imaging techniques to identify the location and extent of damaged tissue that needs to be removed or repaired. In some non-limiting examples, the disclosed fibers may be seeded on both external and luminal surfaces with compatible cells that retain at least some ability to differentiate. In some embodiments, the cells may be autologous cells that may be isolated from the patient (e.g., from the patient bone marrow) or allogeneic cells that may be isolated from a compatible donor. The seeding process may take place in a bioreactor (e.g., a rotating bioreactor) for a few weeks, days, or hours prior to surgery. Additionally, cells may be applied to the polymeric electrospun fibers immediately before implantation. Additionally, one or more growth factors may be added to the composition comprising the polymeric electrospun fibers immediately prior to surgery. The polymeric electrospun fibers incorporating such cells and/or additional chemical factors may then be transplanted or injected into the patient to repair or replace damaged tissue, or to fill voids. The patient may be monitored following the surgery or injection for signs of rejection or poor function. It should be appreciated that the addition of cells and/or chemical factors to the polymeric electrospun fibers may not be required for every procedure. Any one or more of these procedures may be useful alone or in combination to assist in the preparation and/or transplantation of one or more tissues, or a portion of one or more tissues.

It may be appreciated that a variety of biological structures, tissues, and organs may be replaced or repaired by polymeric electrospun fibers. Some non-limiting examples of such structures may include a trachea, a trachea and at least a portion of at least one bronchus, a trachea and at least a portion of a larynx, a larynx, an esophagus, a large intestine, a small intestine, an upper bowel, a lower bowel, a vascular structure, a nerve conduit, cartilage, a meniscus, a ligament, a tendon, a joint, a muscle, the skin, a sphincter, a blood vessel, and portions thereof.

Polymeric Electrospun Fiber Fragments and Clusters

Fibers may be processed into fragments and/or clusters. Such fragments or clusters may be initially prepared by the processes described herein, followed by freezing, for example in liquid nitrogen. Freezing the polymeric electrospun fibers may result in increased brittleness, resulting in fibers that may be readily pulverized into small fragments. Pulverization techniques may include, without limitation, grinding, chopping, pulverizing, micronizing, milling, shearing, or any combination thereof. Fragments may have an average length of about 10 µm to about 1000 µm. In one non-limiting example, fragments may have an average length of about 100 µm. Such fragments may also be compressed into fiber compositions. In one non-limiting example, the compressed fiber composition may be pelletized, or otherwise formed into a compressed or pellet-like structure. Such fragments or clusters may be either resorbable or non-resorbable, or a combination thereof. Fragments may have an average length of about 1 µm to about 1000 µm. In one non-limiting example, fragments may have an average length of about 100 µm. Clusters may have a range of shapes. Non-limiting examples of cluster shapes include spherical, globular, ellipsoidal, and flattened cylinder shapes. Clusters may have, independently, an average length of about 1 µm to about 1000 µm, an average width of about 1 µm to about 1000 µm, and an average height of about 1 µm to about 1000 µm, and may include an average number of about 2 to about 1000 fiber fragments. In one non-limiting example, clusters may include an average number of about 100 fiber fragments. In some embodiments, the polymeric electrospun fiber fragments and/or clusters may be used to retain or localize cells or other components incorporated therewith, to promote cell infusion, attachment, adhesion, penetration, or proliferation, to stimulate cell or tissue growth, healing, or, in some cases, shrinkage, or any combination of uses thereof.

Such polymeric electrospun fiber fragments and/or clusters may be added to a carrier medium to produce a composition for injection or delivery to a body part or system. The composition may have a volume of about 0.1 mL to about 50 mL. The composition may also comprise polymeric electrospun fiber fragments and/or clusters in a weight percent to carrier medium of about 0.001 wt % to about 50 wt %. In some non-limiting examples, the carrier medium may be phosphate buffered saline, normal saline, cell culture media, platelet-rich plasma, plasma, bone marrow, concentrated bone marrow, stromal vascular fraction, lactated Ringer's solution, a gel, a powder, an aerosol, or any combination thereof. In some non-limiting examples, the carrier medium may include an effective amount of chitosan. In some non-limiting examples, the composition may be injected into a joint. Non-limiting examples of joints in which the composition may be injected may include the knee, the shoulder, and the hip. In one non-limiting example, the composition may be injected using a syringe with a 21-gauge needle. In some non-limiting examples, the composition may be injected into a tendon or ligament. In some non-limiting examples, the composition may be injected intravenously, intramuscularly, subcutaneously, or intraperitoneally. In some non-limiting examples, the composition may be delivered topically. In one non-limiting example, the composition may be applied topically to a wound. In some non-limiting examples, the composition may be inserted during surgery. In some non-limiting examples, the composition may be delivered by ingestion, inhalation, or suppository. In some non-limiting examples, the composition may be printed into a construct, or scaffold. In one non-limiting example, the composition may be printed, such as via a three-dimensional printer, for eventual application in a subject or a portion thereof.

A localized injection of a composition of polymeric electrospun fiber fragments and/or clusters may be useful for repair of joint structures, such as a knee meniscus, cruciate ligament, or articular cartilage. Alternatively, such a composition may be used to reduce local joint inflammation, such as inflammation caused by arthritis. In some alternative embodiments, a therapeutically effective compound may be loaded onto or incorporated into the polymeric electrospun fiber fragments and/or clusters themselves. In some alternative embodiments, an injection of a composition of polymeric electrospun fiber fragments and/or clusters may be used to repair localized tissue injuries such as muscle tears, ligament tears, and tendon tears. Muscle injuries that may be repaired by such a composition may include injuries to striated muscle, smooth muscle, and cardiac muscle. It may be appreciated that such polymeric electrospun fiber fragments and/or clusters may be used for such purposes in humans as well as in non-human animals, such as for veterinary applications.

Administering a composition of polymeric electrospun fiber fragments and/or clusters may also be useful for increasing the lubricity of a joint or a tissue, or a portion thereof. In addition, administering a composition of polymeric electrospun fiber fragments and/or clusters may be useful for improving the shock absorption of a joint or a tissue, or a portion thereof. Such applications may be used, for example, in the cartilage or synovium of an articular joint, in order to, for example, improve joint lubrication, or prevent joint inflammation or degradation.

A composition of polymeric electrospun fiber fragments and/or clusters may also be administered to fill voids, such as those found beneath skin wrinkles. Alternatively, such a composition could be used to fill voids, such as sphincter voids associated with anal, colon, urinary, or other types of incontinence. Such applications may be used, for example, for medical, treatment, cosmetic, aesthetic, or any other purpose or combination of purposes. In some alternative embodiments, a localized injection of such a composition could be used as a bulking agent in muscles. In some alternative embodiments, administering such a composition could be used as an anti-wrinkle agent injected beneath the skin.

Administering a composition of polymeric electrospun fiber fragments and/or clusters may also be used as an embolization agent, such as in association with an aneurysm or tumor. In one non-limiting example, administering such a composition, optionally combined with or otherwise added to cells, such as platelet-rich plasma, may be used to occlude an aneurysm of any blood vessel, including those of the brain, heart, and other major organs. In another non-limiting example, administering such a composition, optionally combined with or otherwise added to cells, such as platelet-rich plasma, may be used to occlude all or a portion of one or more whole blood vessels in order to modify or prevent blood flow to a portion of the body, such as a tumor.

A composition of polymeric electrospun fiber fragments and/or clusters may also be used as a material on which or in which cells may incubate, adhere, grow, proliferate, and/or differentiate, as opposed to combining previously grown or expanded cells with a previously created composition of polymeric electrospun fiber fragments and/or clusters. In a non-limiting example, a composition of polymeric electrospun fiber fragments and/or clusters may be used as a material for the incubation, growth, proliferation, and/or differentiation of cells in vitro, followed by injection or implantation in vivo, as opposed to growing cells on polymer microcarriers, releasing the cells from the microcarriers, separating the cells from the microcarriers, and then implanting the cells in vivo. In some embodiments, such an application would reduce or eliminate the need to process cells between culture and implantation, thereby improving cell yield and reducing waste of any cells or materials used in cell growth or proliferation.

In some embodiments, a method of treatment may comprise injecting, into a portion of a body, a composition comprising a plurality of polymeric electrospun fiber fragments and a carrier medium comprising an effective amount of chitosan, as described herein. In other embodiments, the composition may further comprise a plurality of polymeric electrospun fiber fragment clusters. In additional embodiments, the portion of the body may comprise, for example, a portion of one or more of cartilage, a meniscus, a ligament, a tendon, a joint, a muscle, a portion of skin, a sphincter, and a blood vessel. In some embodiments, the method of treatment may be directed to treating, for example, joint inflammation, osteoarthritis, a tissue injury, a muscle tear, a ligament tear, a tendon tear, a void, incontinence, an aneurysm, and a tumor or other growth.

In one embodiment, a method of preparing a composition comprising a plurality of polymeric electrospun fiber fragments and a carrier medium comprising an effective amount of chitosan, as described herein, may include a number of steps. The steps may include harvesting or otherwise preparing a suspension of biological cells such as platelet-rich plasma, bone marrow, or stromal vascular fraction, for example. The steps may also include transferring the suspension of biological cells to a vial or tube containing polymeric electrospun fiber fragments, and, optionally, polymeric electrospun fiber fragment clusters. The concentration of the fragments and, optionally, clusters within the suspension of biological cells may be, for example, about 2 mg/mL. The steps may further include drawing the resulting suspension of fragments, cells, and, optionally, clusters, in and out of a syringe or equivalent one or more times to ensure proper mixing of the components. The resulting suspension may then be left to stand at room temperature for about 30 minutes, rotating it occasionally to ensure uniform coverage. An additional step may include drawing the resulting suspension into a needle and/or syringe for injection into a portion of a body, as described herein.

The above-described compositions of polymeric electrospun fiber fragments and/or clusters may include additional components along with the carrier medium. Non-limiting examples of additional bioactive components may include antibiotics, drugs, tissue growth factors, platelet-rich plasma, bone marrow, concentrated bone marrow, stromal vascular fraction, amnion, small molecules, or any combination thereof. Biologically active cells may also be included in the compositions. Biologically active cells may include differentiated cells, stem cells, or any combination thereof. Such biologically active cells may be added to the compositions to provide cells for improved repair of injured or stunted tissues. Stem cells may include multipotent stem cells, pluripotent stem cells, and totipotent stem cells. Such stem cells may be autologous (from the same patient), syngeneic (from an identical twin, if available), allogeneic (from a non-patient donor), or any combination thereof. In some non-limiting embodiments, the stem cells may include adult stem cells such as bone marrow-derived stem cells, cord blood stem cells, or mesenchymal cells. Other types of stem cells may include embryonic stem cells or induced pluripotent stem cells. It may be appreciated that a composition of polymeric electrospun fiber fragments and/or clusters in a carrier medium may incorporate adult stem cells, embryonic stem cells, induced pluripotent stem cells, differentiated cells, or any combination thereof.

In some embodiments, the above-described compositions of polymeric electrospun fiber fragments and/or clusters may include a carrier medium that includes an effective amount of chitosan. When chitosan is added to a composition of polymeric electrospun fiber fragments and/or clusters, it may exhibit a synergistic effect that radically enhances the healing capacity of those polymeric electrospun fiber fragments and/or clusters. In one non-limiting example, the addition of chitosan is advantageous for the treatment of osteoarthritis (OA). The use of chitosan in a composition of polymeric electrospun fiber fragments and/ or clusters surprisingly allows for a significant increase in the concentration of polymeric electrospun fiber fragments and/or clusters in the composition without increased aggregation or clumping of those polymeric electrospun fiber fragments and/or clusters. As a result, the injection or dispersion of polymeric electrospun fiber fragments and/or clusters may be drastically improved by using chitosan to enhance these compositions. Cells may tightly attach to the chitosan and polymeric electrospun fiber fragments and/or clusters to form micromasses, which grow into cartilage-like nodules.

Polymeric electrospun fiber fragments and/or clusters may be combined with other carrier materials, and are not limited to purely aqueous compositions. In some other non-limiting embodiments, polymeric electrospun fiber fragments and/or clusters may be combined with gels, pastes, powders, aerosols, and/or other carriers. In one non-limiting example, the fiber fragments and/or clusters may be combined with a carrier capable of forming a gel, solid, powder, or aerosol when implanted into a subject (human or non-human animal). Gelation or solidification of the carrier may occur on exposure of the composition to the biological environment due, for example, to a change in temperature or pH. Alternative carriers may include components capable of responding to externally applied stimuli such as magnetic fields, electric fields, or sonic fields. In one non-limiting example, a carrier may respond to an applied magnetic field to cause the fragments to orient in a specific direction. Polymeric electrospun fiber fragments and/or clusters without a carrier may also be implanted in a recipient. In one non-limiting application, polymeric electrospun fiber fragments and/or clusters may be implanted directly into a solid tumor. The implanted fragments and/or clusters may concentrate externally applied heat, sonic, or radiation energy to the tumor. In one non-limiting example, polymeric electrospun fiber fragments and/or clusters may be implanted for the purpose of localized or systemic delivery of drugs, biological materials, contrast agents, or other materials, as disclosed above.

In one non-limiting example, polymeric electrospun fiber fragments and/or clusters may be sold in a kit. In a non-limiting example, the kit may further comprise a carrier medium, which may comprise an effective amount of chitosan. In a non-limiting example, the kit may further comprise instructions for the use of the polymeric electrospun fiber fragments, clusters, and/or carrier medium, which may comprise an effective amount of chitosan. In a non-limiting example, the carrier medium may be any of the above-disclosed carrier media, in any form, including, for example, a gel, a dry form such as a powder, an aerosol, a liquid, or any other form, including those which may be reconstituted for use.

In order to illustrate the various features disclosed above, the following non-limiting examples are provided.

EXAMPLES

Example 1

Polymeric Electrospun Fiber Fragments

Figure 1B:
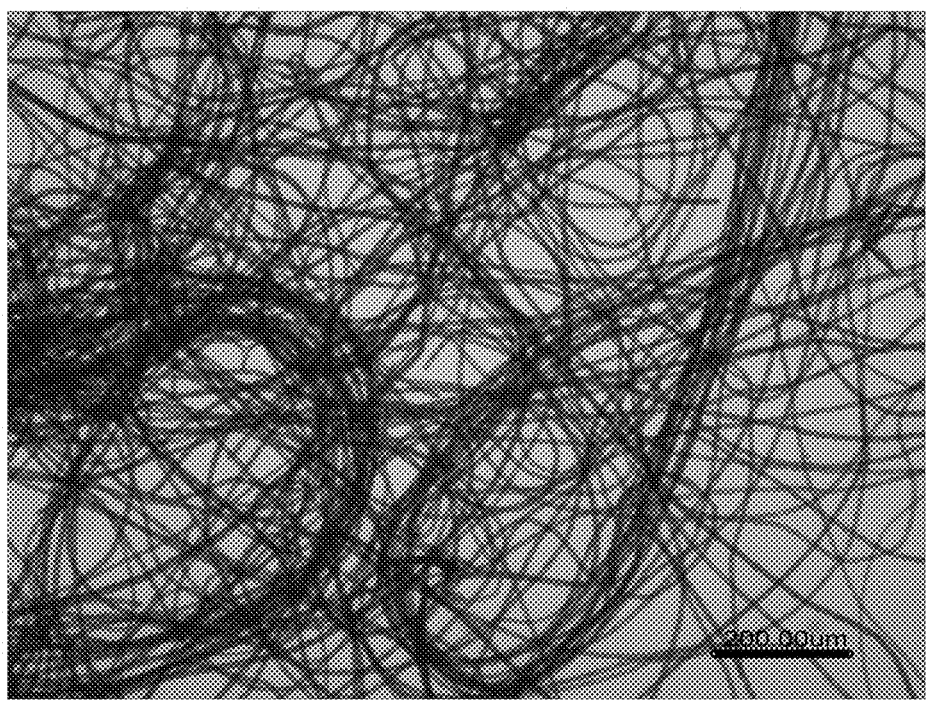

FIGS. 1A and 1B depict images of polymeric electrospun fiber fragments dispersed in water. The fragments were prepared by a standard electrospinning approach and then cryosheared. Briefly, 8 wt % polylactide-co-glycolide (PLGA) was dissolved in hexafluoro isopropanol and electrospun into a highly aligned mat. The mat was then cut into approximately 5 mm×5 mm pieces and placed in liquid nitrogen. A shear mixer was then placed in the liquid nitrogen at approximately 30,000 RPM for 1 minute to micronize the fibers. In an alternative method, the 5 mm×5 mm pieces may be pushed with dry ice into a rotary shear machine that subsequently cuts them into small fragments. FIG. 1A depicts a low power magnification (40×) view, and FIG. 1B depicts a high power magnification (100×) view of the polymeric electrospun fiber fragments. The polymeric electrospun fiber fragments depicted in FIGS. 1A and 1B had an average diameter of 500 nm and an average length of about 500 μm.

Figure 2A:
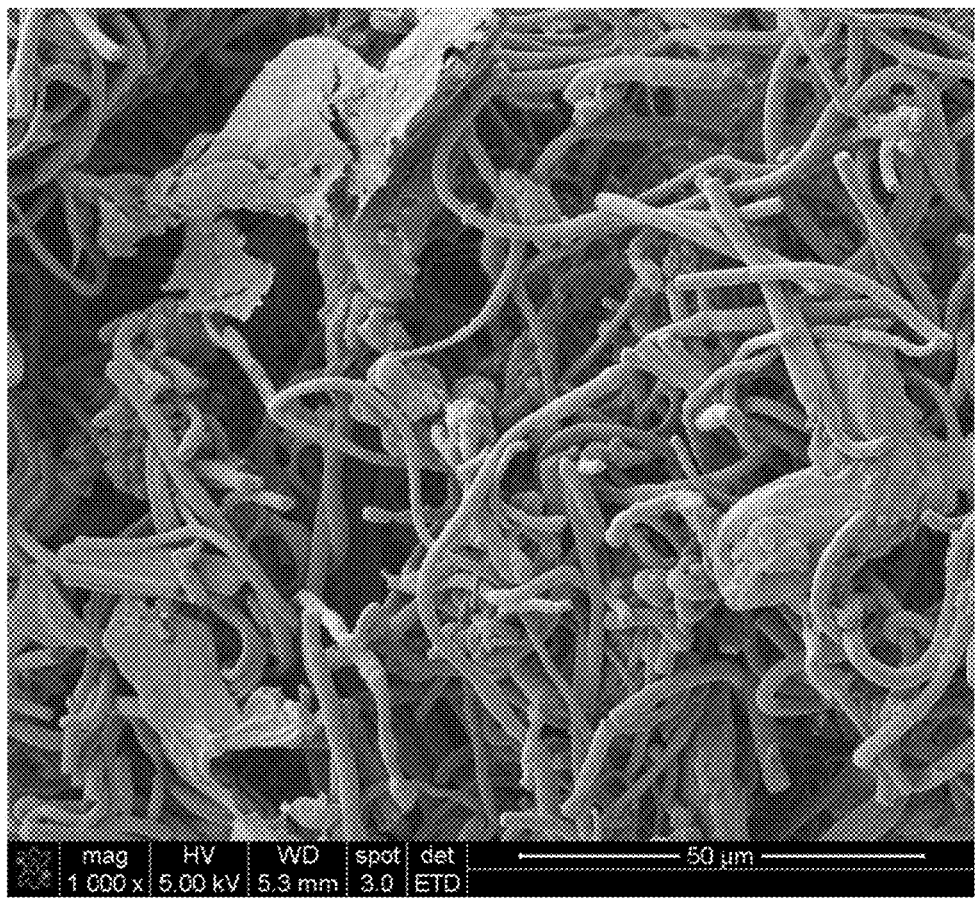
FIGS. 2A, 2B, 2C, and 2D depict scanning electron microscope images of polymeric electrospun fiber fragments when exposed to adipose-derived stem cells, at 0 minutes after exposure to stem cells, at 5 minutes after exposure to stem cells, at 25 minutes after exposure to stem cells, and at 30 minutes after exposure to stem cells, respectively, in accordance with the present disclosure.
Figure 2B:
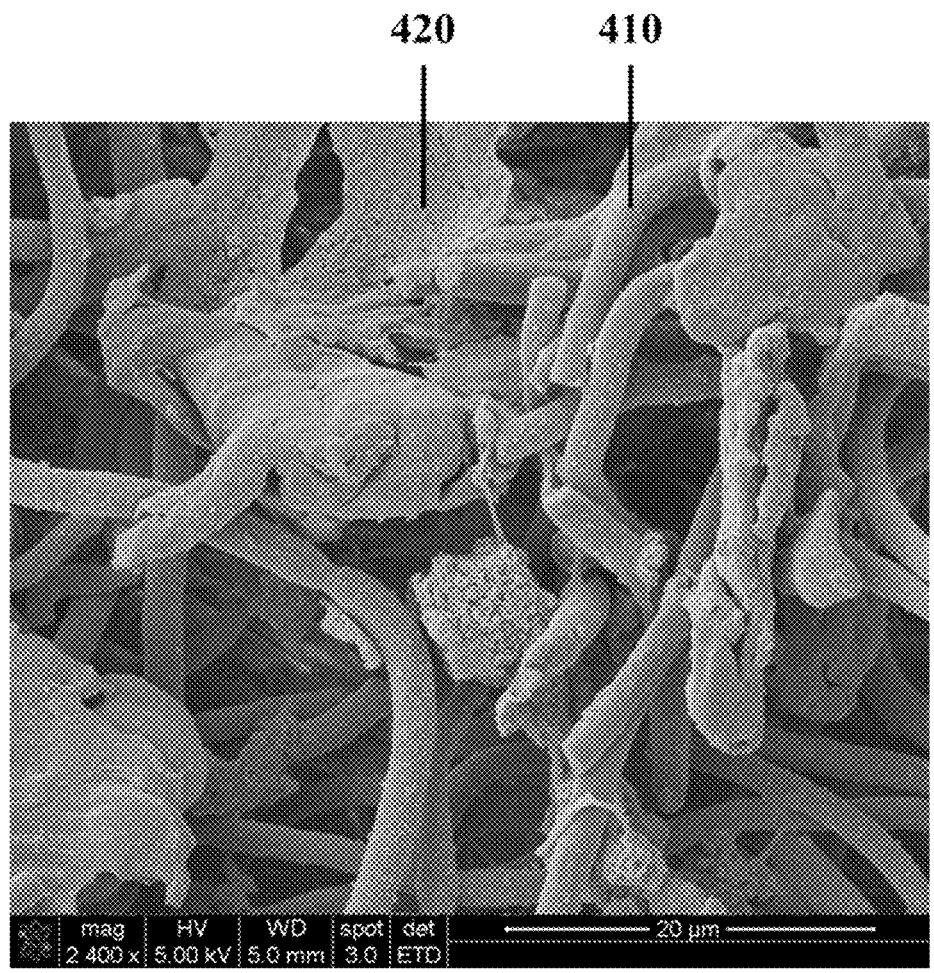
Figure 2C:
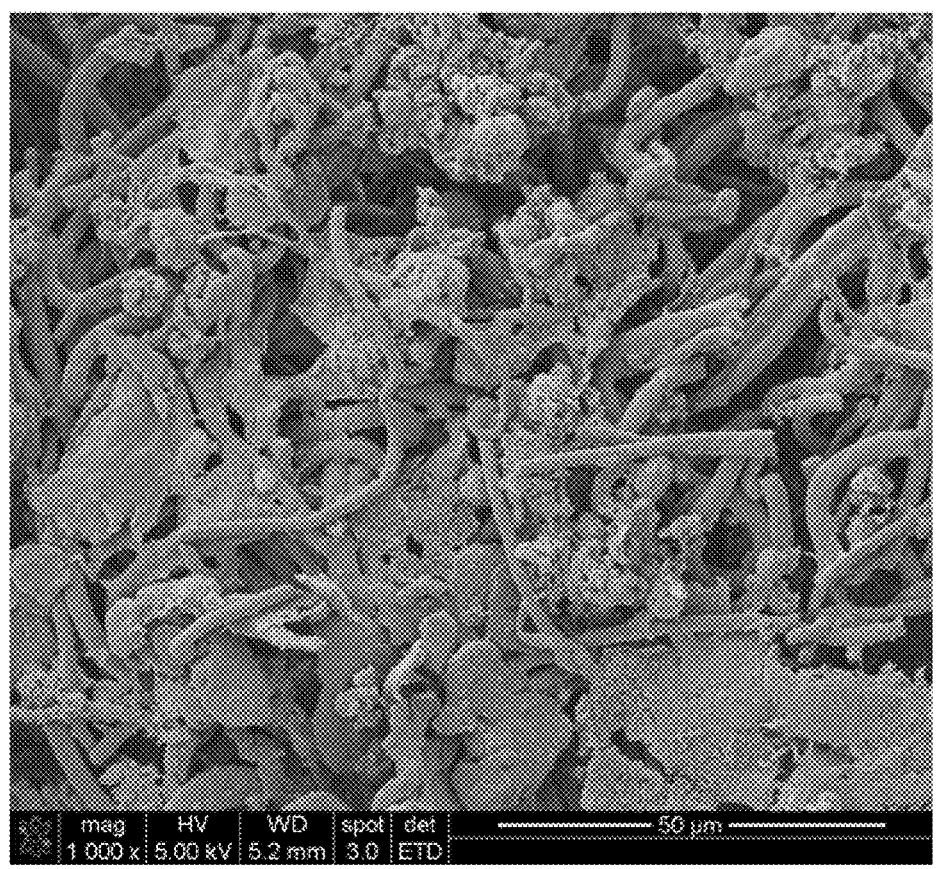
Figure 2D:
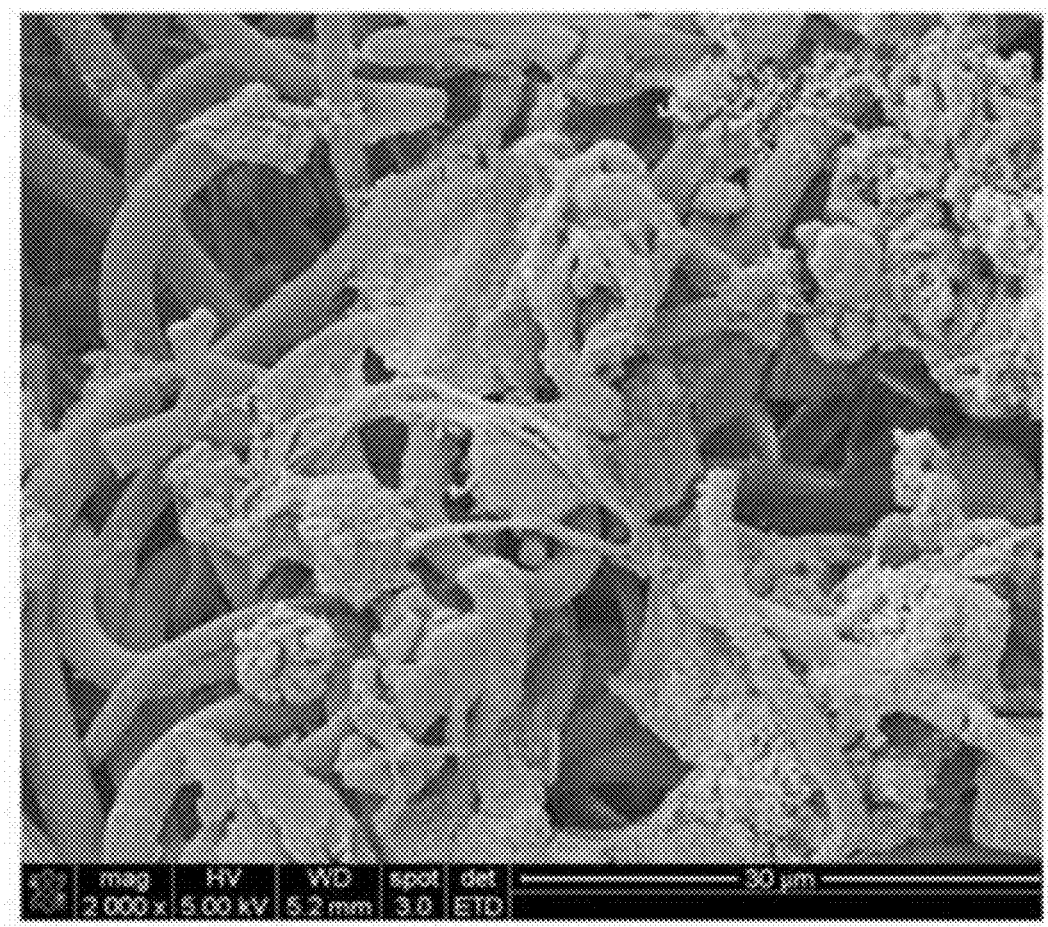
Figure 3:
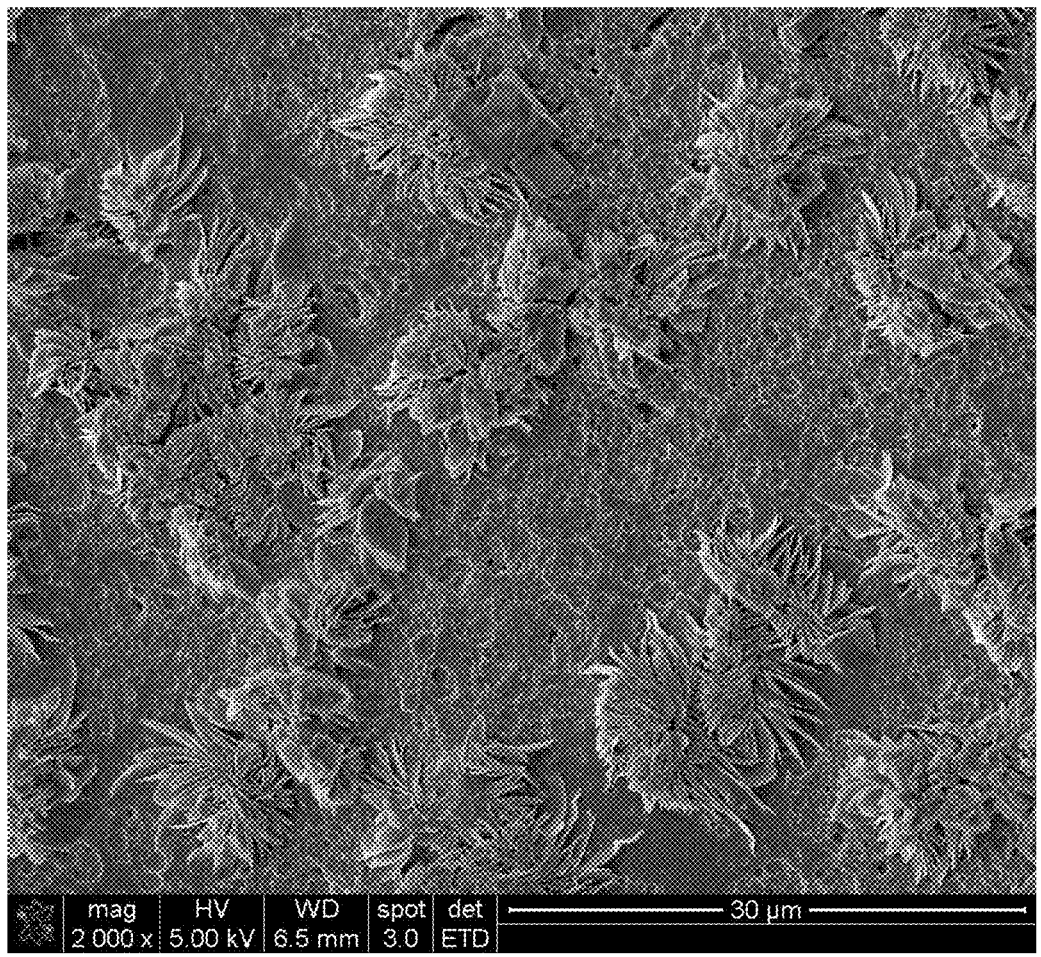
FIG. 3 depicts a scanning electron microscope image of platelet-rich plasma combined with polymeric electrospun fiber fragments at 0 minutes after exposure. The polymeric electrospun fiber fragments, or "nanowhiskers," are barely visible, due to the rapid attachment of platelets to the fibers.
Figure 4A:
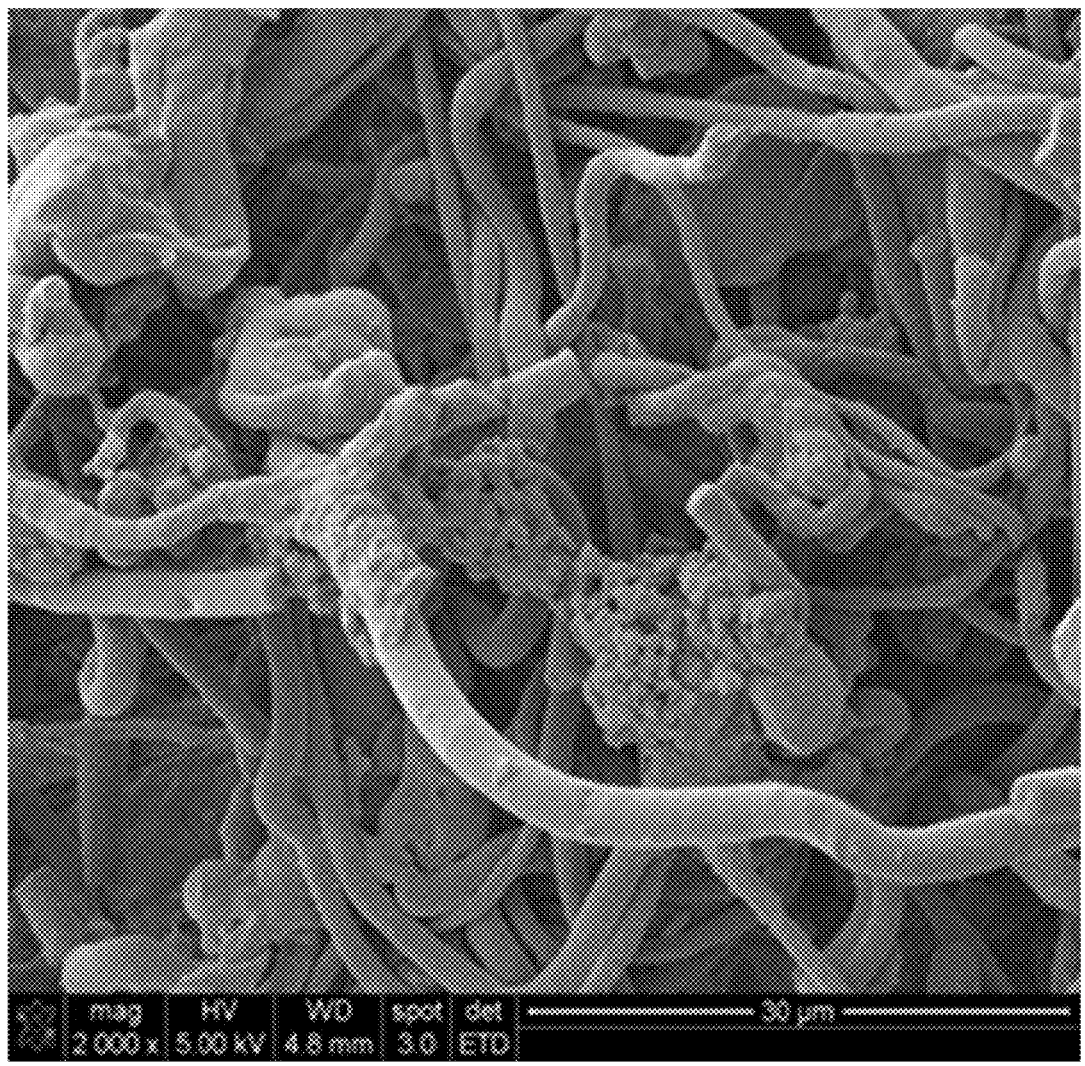
FIGS. 4A, 4B and 4C depict scanning electron microscope images of polymeric electrospun fiber fragments when exposed to adipose-derived stem cells, at 30 minutes after exposure to stem cells, at 60 minutes after exposure to stem cells, and at 120 minutes after exposure to stem cells, respectively, in accordance with the present disclosure.
Figure 4B:
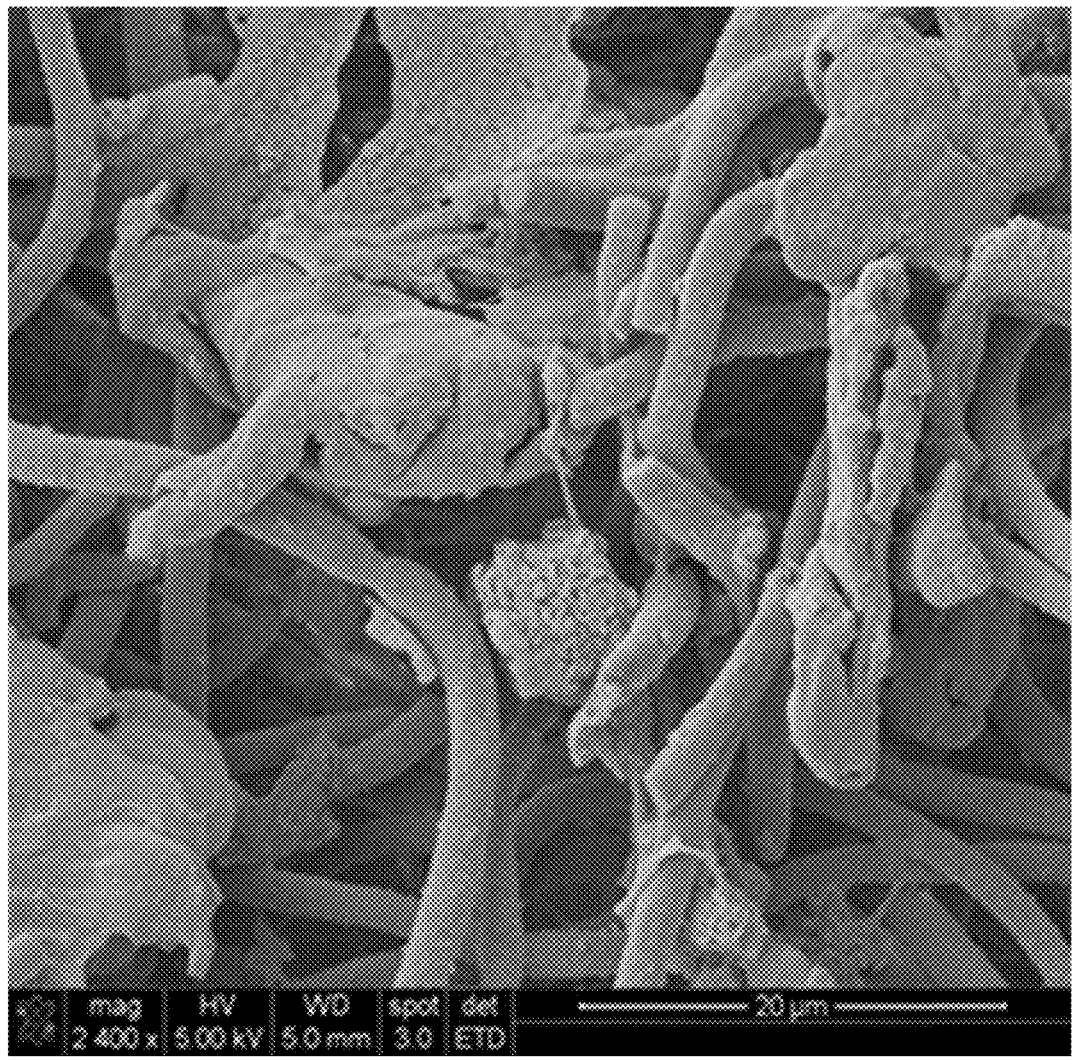
Figure 4C:
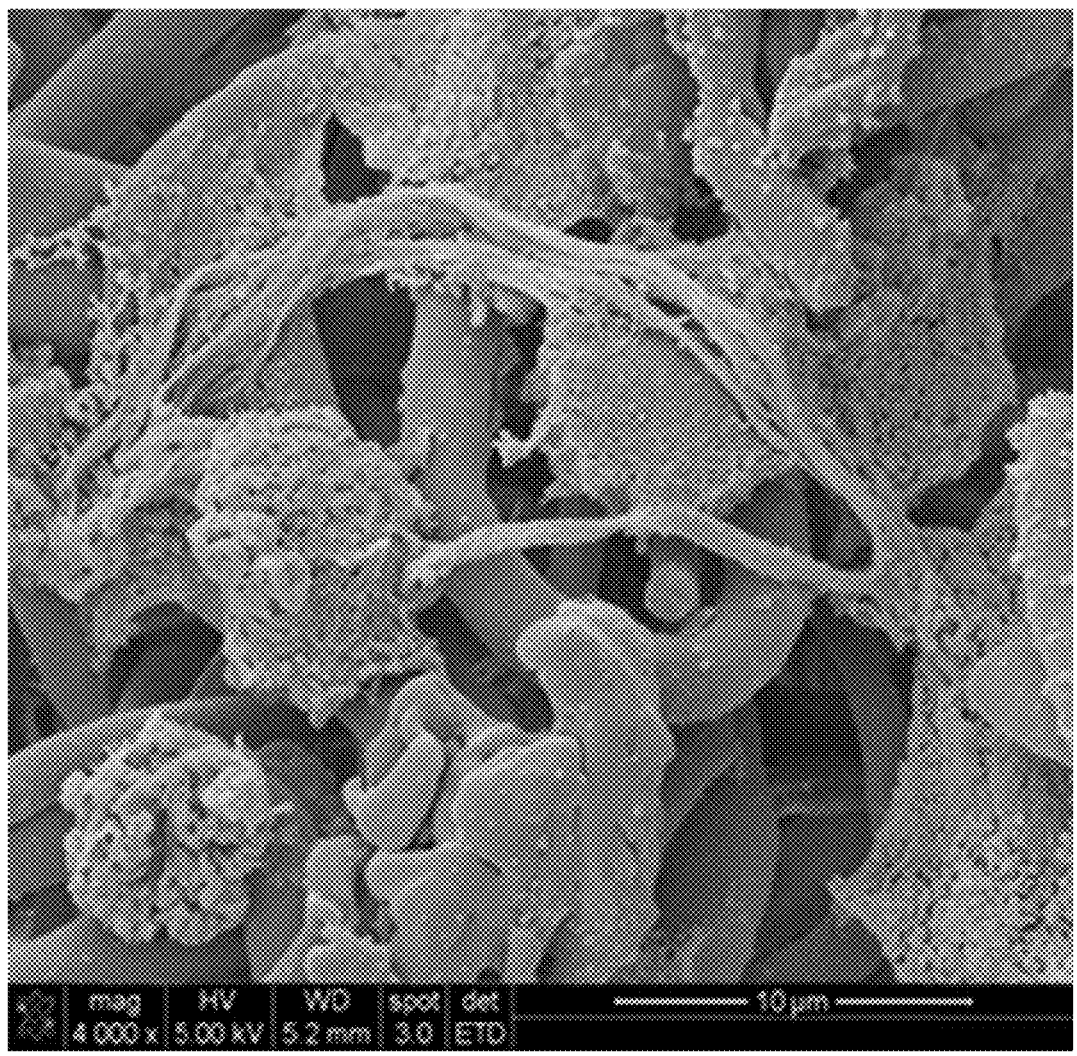
Figure 5:
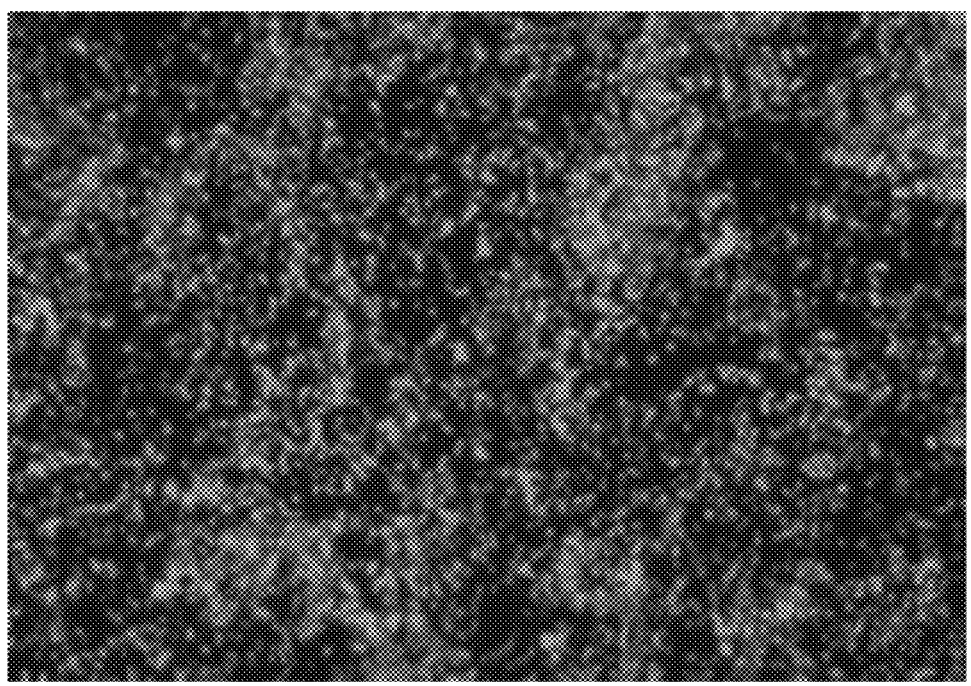
FIG. 5 depicts a quantification of cell expansion on polymeric electrospun fiber fragments with fluorescent microscopy, in accordance with the present disclosure.
Figure 6:
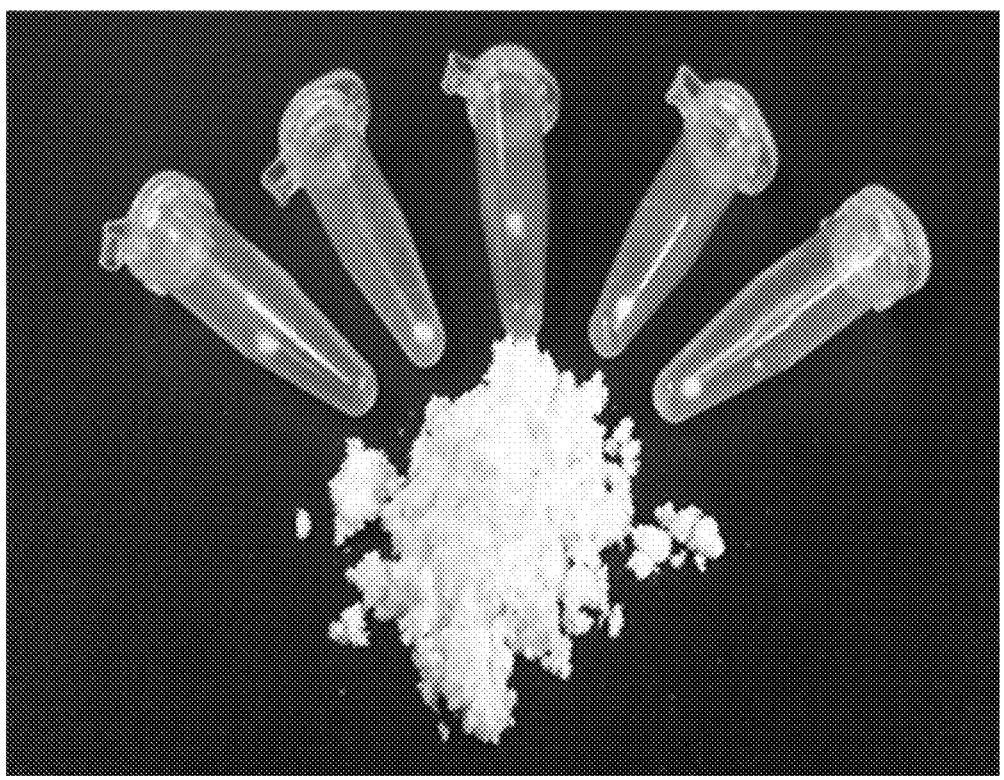
FIG. 6 depicts an embodiment of polymeric electrospun fiber fragments in accordance with the present disclosure.
Figure 7A:
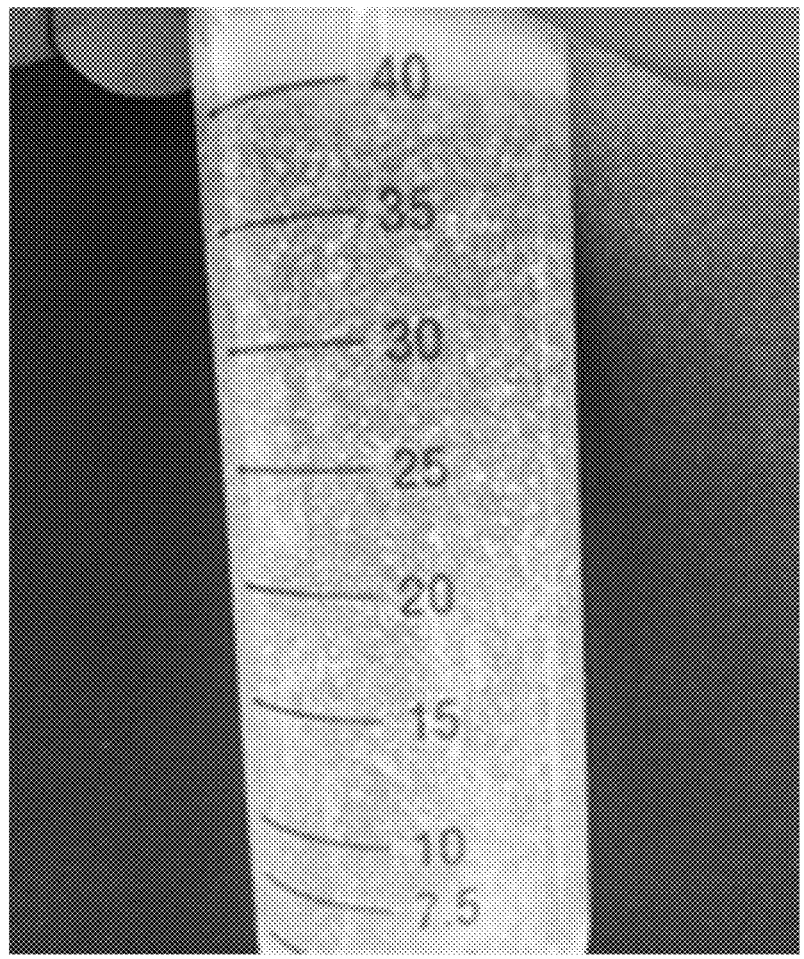
FIGS. 7A, 7B, and 7C depict polymeric electrospun fiber fragments dispersed in cell culture media at concentrations of 2 mg/mL, 5 mg/mL, 15 mg/mL, respectively, in accordance with the present disclosure.
Figure 7B:
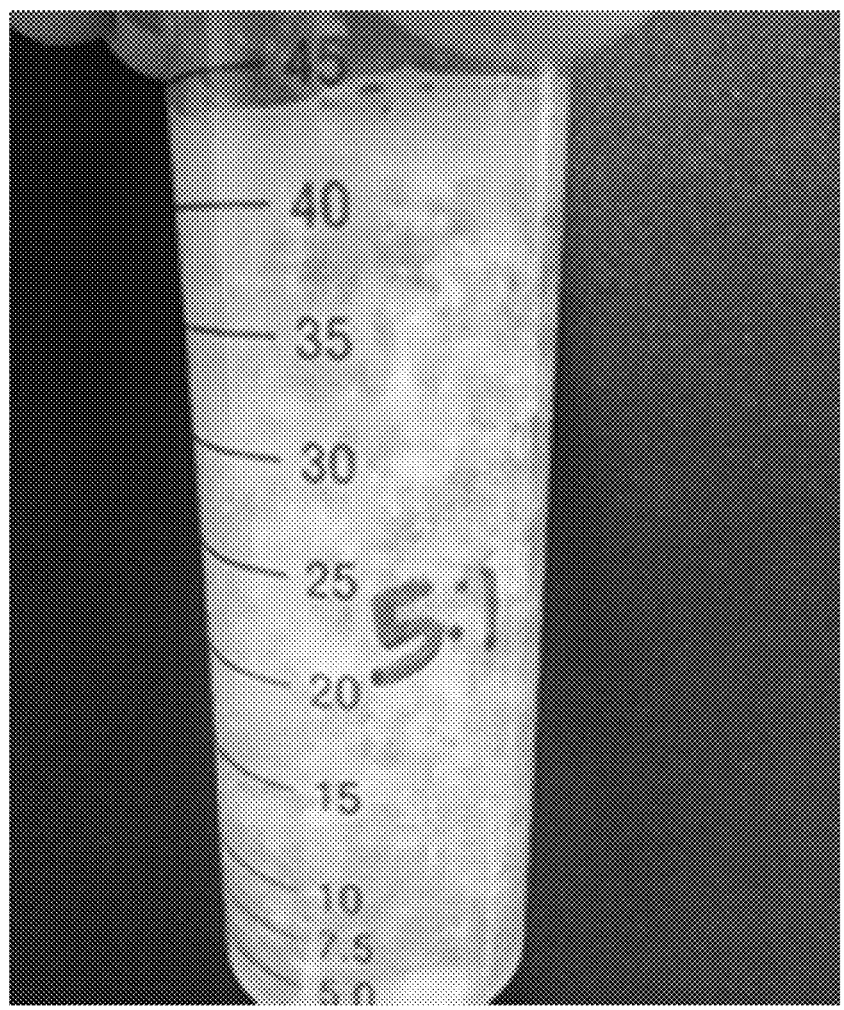
Figure 7C:
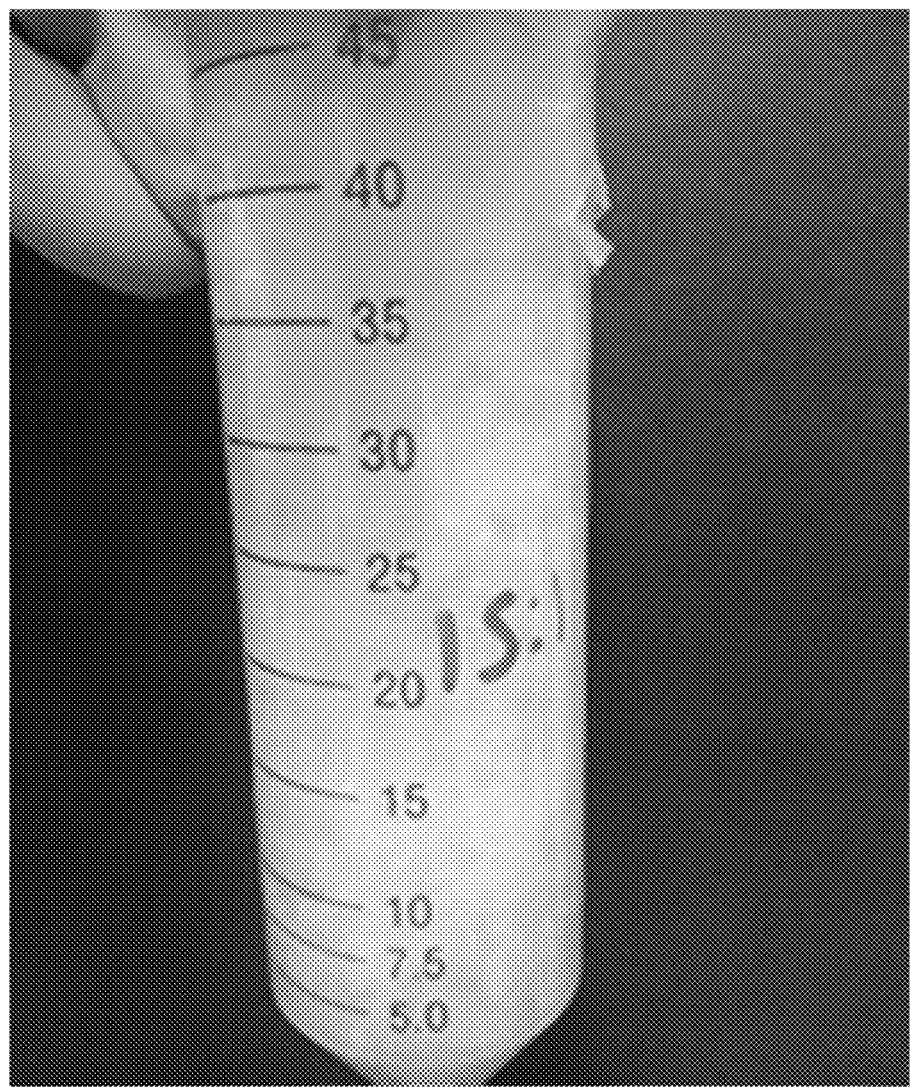

Approximately 1.5 mg of micronized fiber fragments of PLGA fibers (500 nm diameter, 500 μm length) was mixed with adipose-derived mesenchymal stem cells using the stromal vascular fraction suspended in phosphate buffered saline and maintained at room temperature for up to four hours. FIG. 2A depicts a micrograph of the composition of micronized fiber fragments immediately after the addition of the stem cells. FIG. 2B depicts the same preparation as FIG. 2A after an incubation time of about 5 minutes, and shows a cluster of fiber fragments 210, and a cell embedded in the composition of micronized fiber fragments 220. FIG. 2C depicts the same preparation after an incubation time of about 15 minutes, and FIG. 2D depicts the same preparation after an incubation time of about 30 minutes. It may be observed that the stem cells quickly attach, proliferate, and produce extracellular matrix on the fibers, and appear to totally cover the fiber fragments in about 2 hours.

Example 2

Polymeric Electrospun Fiber Loadings and Syringe Tip Gauges

In an experiment, 1.5 mL vials loaded with polymeric electrospun fiber fragments and clusters, or "nanowhiskers," as described above, were filled with 1 mL phosphate buffered saline (PBS). No chitosan was added to the composition. Using a 20 cc syringe, the composition of polymeric electrospun fiber fragments and clusters was pulled out of the vial and into the syringe. The syringe and empty vial were both inspected for the presence of the polymeric electrospun fiber fragments and clusters, and the composition was then injected back into the vial. The full vial and empty syringe were then both inspected for the presence of the polymeric electrospun fiber fragments and clusters. This procedure was repeated for each loading, using syringe tips with progressively smaller diameters. Syringe tips were flushed with isopropanol, followed by PBS, between each test.

At fiber fragment and/or cluster concentrations of 1 mg/mL, 2 mg/mL, 3 mg/mL, 5 mg/mL, 10 mg/mL, and 15 mg/mL, with an at least 18-gauge syringe tip, and at 1 mg/mL, 2 mg/mL, 3 mg/mL, 5 mg/mL, and 10 mg/mL, with an at least 20-gauge syringe tip, and 1 mg/mL and 2 mg/mL with at least a 23-gauge syringe tip, the composition with polymeric electrospun fiber fragments and clusters completely passed into and out of the syringe tip. No fiber material was left on the syringe tip when the composition was pulled into the syringe, and little or no fiber material was left inside the syringe after the composition had been injected back into the vial.

At fiber fragment and/or cluster concentrations of 15 mg/mL with at least an 18-gauge syringe tip, and 3 mg/mL with at least a 23-gauge syringe tip, some fiber material passed into and out of the syringe tip. A significant amount of fiber material was left around the outside of the tip after the composition was pulled into the syringe, and a significant amount of fiber material was left inside the syringe after the composition was injected back into the vial.

At fiber fragment and/or cluster concentrations of 5 mg/mL, 10 mg/mL and 15 mg/mL with at least a 23-gauge syringe tip, very little or no fiber material passed through the syringe tip as the solution was pulled into the syringe and/or injected out of it. After the composition was pulled into the syringe, most of the fiber material was left behind in the vial. After the composition was injected out of the syringe, most of the fiber material was left behind in the syringe. Fiber material may have clogged the syringe during any step.

In contrast to the above-described results observed with fiber fragment and/or cluster compositions without chitosan added, with a fiber fragment and/or cluster composition that includes from about 0.001 wt % to about 5 wt % chitosan to carrier medium, concentrations from about 10 mg/mL to about 15 mg/mL are easily passed through at least a 21-gauge syringe tip. These results are surprising and unexpected, and demonstrate a synergistic effect that occurs when chitosan is added to a composition of fiber fragments and/or clusters in a carrier medium. Without wishing to be bound by theory, chitosan may coat the polymeric electrospun fiber fragments and/or clusters to increase the concentrations at which they may pass through a small needle, improve the viscosity of the carrier medium of the composition which includes polymeric electrospun fiber fragments and/or clusters, improve the wetting of the polymeric electrospun fiber fragments and/or clusters, improve the surface interaction of the polymeric electrospun fiber fragments and/or clusters with each other and/or with the carrier medium, or exhibit this surprising synergistic effect by any other mechanism.

Example 3

Polymeric Electrospun Fiber Implantation in Equine Subjects

The injection of a composition of polymeric electrospun fiber fragments and clusters, as demonstrated in FIGS. 2A, 2B, 2C, and 2D, which did not contain chitosan, was examined in three equine subjects. The first equine subject was a 23-year-old male quarter horse with a history of chronic bilateral front foot pain that did not respond to conventional treatment. The pain was consistent with caudal foot pain and navicular syndrome. On the day of the procedure, the first equine subject was evaluated for lameness, and scored a 3/5 on the American Association of Equine Practitioners (AAEP) lameness scale.

The second equine subject was a 23-year-old male quarter horse who scored 1/5 on the AAEP lameness scale after an acute soft tissue injury to his left stifle joint. The second equine subject showed minimal response to conventional joint therapies prior to the procedure.

The third equine subject was a 20-year-old female quarter horse with a history of chronic degenerative joint disease in her hind limbs, which showed limited response to conventional therapies. She scored 1/5 on the AAEP lameness scale at the trot, and 4/5 after stifle flexion.

Blood was drawn and adipose tissue was harvested from the rump of each subject. The adipose samples were incubated in a hot water bath, and stem cells were isolated using enzymatic digestion, centrifugation, and a vacuum-powered sieve. Platelet-rich plasma was isolated from the blood samples via centrifugation, and was added to the adipose stem cell compositions. These compositions were placed in an LED stem cell activation device, which activated the cells to more quickly begin the repair process upon re-implantation. Stem cell compositions were then removed from the LED device, and placed in sterile vials with a concentration of 2 mg polymeric electrospun fiber fragments and clusters per 1 mL cell composition. These vials were gently agitated to disperse the fibers in the stem cell solution, and then left to sit for 15 minutes to allow the autologous stem cells to adhere to the polymeric electrospun fiber fragments and clusters. No chitosan was added to the compositions. The resultant compositions were drawn into sterile syringes with 20-gauge needle tips for injection into the joints.

The first equine subject received injections in each of his front coffin joints. The second equine subject received an injection in the medial femorotibial joint of his left stifle. The third equine subject received injections in the medial femorotibial joints of both stifles. All three horses were treated with phenylbutazone for 4 days following the procedure. After 30 days, each horse was re-evaluated. The first equine subject improved from a 3/5 score to a 1/5 score on the AAEP lameness scale, the second equine subject scored slightly less than 1/5 with a 50% improvement in flexion, and the third equine subject showed a 25% improvement in stifle flexion. Each subject showed improvements in the lameness and flexion of the affected joints, which surpassed those gained from conventional treatments.

Example 4

Chitosan-Enhanced Electrospun Fiber Implantation in a Canine Subject

The injection of a composition comprising polymeric electrospun fiber fragments polymeric electrospun fiber fragment clusters, and a carrier medium comprising chitosan, as demonstrated in FIGS. 2A, 2B, 2C, and 2D, was examined in a canine subject. The patient, Gussie, was an 11-year-old female Vizsla with a history of chronic stifle pain and stiffness that did not respond to conventional treatment. The dog was unable to run due to the pain, and could only move in a slow, painful walk with a severe limp. X-rays confirmed arthritic lesions in the dog's hip joints.

0.5 mL of the chitosan-enhanced composition suspended in saline was injected intraarticularly into each stifle. The dog was sore and stiff in the injected joints for almost two weeks after the procedure, but then regained her mobility and began improving in her gait. Gussie could walk without a limp and with a normal gait after one month. After 6 months, Gussie returned to the veterinarian for a follow-up appointment. The veterinarian performed a gait analysis and noted significant improvement in gait, stance, and overall mobility with no detectable limp. X-rays were taken to document the improvement of the arthritic lesions in the joints. This case demonstrates the therapeutic function of a chitosan-enhanced polymeric electrospun fiber fragment composition as described herein to provide a therapeutic benefit without additional biological cells or suspensions thereof included prior to injection.

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the applicant's general inventive concept.

The invention claimed is:

1. A composition comprising:

a plurality of synthetic polymeric electrospun fiber fragments; and an aqueous carrier medium comprising an effective amount of chitosan;

wherein the plurality of synthetic polymeric electrospun fiber fragments are present in an amount from about 1 fragment per mm$^3$ to about 100,000 fragments per mm$^3$; and wherein the effective amount of chitosan to the aqueous carrier medium is from about 0.0001 wt % to about 5 wt %.

2. The composition of claim 1, further comprising a plurality of synthetic polymeric electrospun fiber fragment clusters.

3. The composition of claim 2, wherein the plurality of synthetic polymeric electrospun fiber fragment clusters have, independently, an average length of about 1 µm to about 1000 µm, an average width of about 1 µm to about 1000 µm, and an average height of about 1 µm to about 1000 µm.

4. The composition of claim 2, wherein a weight percent of the plurality of synthetic polymeric electrospun fiber fragments and the plurality of synthetic polymeric electrospun fiber fragment clusters to the aqueous carrier medium is about 0.0001 wt % to about 10 wt %.

5. The composition of claim 1, wherein the plurality of synthetic polymeric electrospun fiber fragments have, independently, an average length of about 1 µm to about 1000 µm, and an average diameter of about 0.1 µm to about 10 µm.

6. The composition of claim 1, further comprising at least one biological cell selected from the group consisting of an autologous cell, a syngeneic cell, an allogeneic cell, a differentiated cell, a stem cell, a multipotent stem cell, a pluripotent stem cell, an induced pluripotent stem cell, a totipotent stem cell, a bone marrow-derived stem cell, a cord blood stem cell, a mesenchymal cell, an embryonic stem cell, platelet-rich plasma, stromal vascular fraction, and combinations thereof.

7. A kit comprising:
   a first component comprising a plurality of synthetic polymeric electrospun fiber fragments; and
   a second component comprising an aqueous carrier medium comprising an effective amount of chitosan;
   wherein the plurality of synthetic polymeric electrospun fiber fragments are present in an amount from about 1 fragment per mm$^3$ to about 100,000 fragments per mm$^3$; and
   wherein the effective amount of chitosan to the aqueous carrier medium is from about 0.0001 wt % to about 5 wt %.

8. The kit of claim 7, wherein the first component further comprises a plurality of synthetic polymeric electrospun fiber fragment clusters.

9. A method of treatment comprising injecting, into a portion of a body, the composition of claim 1.

10. The method of claim 9, wherein the composition further comprises a plurality of synthetic polymeric electrospun fiber fragment clusters.

11. The method of claim 9, wherein the portion of the body comprises one or more of a portion of cartilage, a meniscus, a ligament, a tendon, a joint, a muscle, a portion of skin, a sphincter, and a blood vessel.

* * * * *